United States Patent
Huang

(10) Patent No.: US 10,428,373 B2
(45) Date of Patent: Oct. 1, 2019

(54) DUPLICATING DNA WITH CONTIGUITY BARCODES FOR GENOME AND EPIGENOME SEQUENCING

(71) Applicant: The Regents of the University of California, Oakland, CA (US)

(72) Inventor: Xiaohua Huang, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 387 days.

(21) Appl. No.: 15/035,957

(22) PCT Filed: Nov. 13, 2014

(86) PCT No.: PCT/US2014/065491
§ 371 (c)(1),
(2) Date: May 11, 2016

(87) PCT Pub. No.: WO2015/073693
PCT Pub. Date: May 21, 2015

(65) Prior Publication Data
US 2016/0265039 A1    Sep. 15, 2016

Related U.S. Application Data

(60) Provisional application No. 61/904,637, filed on Nov. 15, 2013.

(51) Int. Cl.
*C12Q 1/6869*   (2018.01)
*C12Q 1/6844*   (2018.01)
*B01L 3/00*     (2006.01)

(52) U.S. Cl.
CPC ...... *C12Q 1/6846* (2013.01); *B01L 3/502738* (2013.01); *B01L 3/502753* (2013.01); *C12Q 1/6869* (2013.01); *B01L 2200/0621* (2013.01); *B01L 2200/0631* (2013.01); *B01L 2200/0668* (2013.01); *B01L 2300/0645* (2013.01); *B01L 2300/0681* (2013.01); *B01L 2300/0816* (2013.01); *B01L 2300/0864* (2013.01); *B01L 2400/0421* (2013.01); *B01L 2400/0487* (2013.01); *B01L 2400/0605* (2013.01); *B01L 2400/0666* (2013.01)

(58) Field of Classification Search
None
See application file for complete search history.

(56) References Cited

U.S. PATENT DOCUMENTS

| 2012/0228142 A1 | 9/2012 | Sibbett et al. |
| 2013/0130919 A1 | 5/2013 | Chen et al. |
| 2013/0203605 A1 | 8/2013 | Shendure et al. |

FOREIGN PATENT DOCUMENTS

| WO | 2012061832 A1 | 5/2012 | |
| WO | WO-2012061832 A1 * | 5/2012 | ......... C12N 15/1065 |
| WO | 2012/106546 A2 | 8/2012 | |
| WO | 2013/151803 A1 | 10/2013 | |
| WO | 2014/145820 A2 | 9/2014 | |

OTHER PUBLICATIONS

"IllustraTM GenomiPhi DNA Amplification Kit", GE Healthcare, Retrieved from the Internet: <http://cichlid.umd.edu/cichlidlabs/protocols/Basic/GPHI_V2_25660030_revB.pdf> on Jan. 27, 2015, 2006, pp. 1-22.
"T4 DNA polymerase", Epicentre, Retrieved from the Internet: http://www.epibio.com/docs/default-source/protocols/t4-dna-polymerase.pdf?sfvrsn=6> on Jan. 27, 2015, Jun. 2012, pp. 1-2.
Lee, et al., "Microfluidic devices with permeable polymer barriers for capture and transport of biomolecules and cells", Lab Chip., vol. 13, Jul. 7, 2013, pp. 3389-3397 (renumbered pp. 1-15).
PCT/US2014/065491, "International Search Report and Written Opinion", dated Feb. 23, 2015, 11 pages.
European Partial Supplementary Search Report for EP Application No. EP 14862612 dated May 29, 2017 (21 pages).
Dean et al., "Rapid Amplification of Plasmid and Phage DNA Using Phi29 DNA Polymerase and Multiply-Primed Rolling Circle Amplification," Genome Research, 2001, 11(6):1095-1099.
Fraz et al., "Optimized Library Preparation Method for Next-Generation Sequencing," Nature Methods, 2009, 6(10)I-II.

* cited by examiner

*Primary Examiner* — Kaijiang Zhang
(74) *Attorney, Agent, or Firm* — Eversheds Sutherland (US) LLP

(57) ABSTRACT

Provided herein are methods and devices for accurate sequencing and detection of epigenetic information from template polynucleotides. Also provided are methods for long-range strand displacement amplification of polynucleotides, microfluidic devices with selectively permeable barriers for multistep processing, and methods for polynucleotide amplification using the microfluidic devices.

10 Claims, 13 Drawing Sheets

Adaptors: Sequences for downstream processing, e.g. amplification and sequencing.
Barcode: Unique sequence to confer contiguity or linkage information.
Barcode pair: Two unique complementary sequences.
Primer: Random or semi random nucleic acid sequence for priming.

(A)

(B)

(C)

DUPLICATING DNA WITH CONTIGUITY BARCODES FOR GENOME AND EPIGENOME SEQUENCING

CROSS-REFERENCES TO RELATED APPLICATIONS

This application is a National Stage of International Application No. PCT/US2014/065491, filed Nov. 13, 2014, which claims priority to U.S. Application No. 61/904,637, filed Nov. 15, 2013, the disclosure of which is incorporated by reference in its entirety.

BACKGROUND OF THE INVENTION

The present disclosure is in the field of DNA amplification and sequencing, and microfluidic processing devices. Ideally, genome sequencing can deliver the genome and the epigenome sequence of a single cell with 100% accuracy and end-to-end contiguity at low cost.

It is not clear if current nanopore sequencing technologies can deliver the read lengths, accuracy and throughput for rapid de novo genome sequencing at low cost (Branton et al. 2008; Cherf et al. 2012; Clarke et al. 2009; Kumar et al. 2012; Manrao et al. 2012; McNally et al. 2010; Wallace et al. 2010; Wanunu 2012). Due to the inefficiency in capturing DNA into nanopores (Branton et al. 2008; Wanunu et al. 2010), it would not be feasible to sequence the genome of a single cell without some sample preparation, including fragmentation and amplification. The current generation of sequencers, which are mostly based on sequencing by synthesis using DNA polymerases, are remarkable in terms of sequencing throughput and accuracy (e.g. close to 1 trillion bases per run with 99.9% raw accuracy for most reads for the Illumina HiSeq 2500) despite the relative short reads (a few hundred bases or much shorter). The per-base sequencing cost has also been brought down drastically at rapid pace. However, many technical challenges remain to be overcome to achieve the quality of the genome sequence in terms of per-base accuracy, the contiguity of the assembly and complete phasing of haplotype for personalized medicine (Baker et al. 2012; Marx 2013).

First, the assembly of genomes with highly repetitive sequences using short reads (a few hundred bases or shorter) produced by these high-throughput sequencers is extremely challenging (Baker et al. 2012; Bradnam et al. 2013; Li et al. 2010; Marx 2013; Salzberg et al. 2012; Treangen et al. 2012). De novo sequencing and assembly of diploid genomes with full haplotype resolution is even more difficult. Second, the accuracy that can be achieved with current sequencing technologies is still relatively low (consensus error rate of 1 error in 10 million is the best reported (Peters et al. 2012)). Sequencing errors are primarily due to limitations of the sequencing chemistry, which at best has a raw read accuracy of 99.9% (i.e. an error rate of $10^{-3}$), and errors introduced by the sample preparation process, in particular DNA amplification by DNA polymerases which usually have error rate not better than $10^{-6}$.

Single-cell de novo genome sequencing is even more challenging because the current technologies require DNA input from the equivalent of many cells (20-10,000 depending on the platform) (Kalisky et al. 2011). Yet the ability to sequence the genome of single cells has very important applications in basic biomedical research and even greater impacts on the application of genome sequencing in clinical practices (Kalisky et al. 2011). For example, this allows for the comprehensive characterization of the cellular heterogeneity that underlies normal cellular differentiation and diseases such as cancer (Ma et al. 2012; Navin et al. 2011; Navin et al. 2011; Potter et al. 2013; Powell et al. 2012), the very early detection of cancer using circulating tumor cells or fine needle biopsies, mutation detection (Lu et al. 2012; Wang et al. 2012), for the genetic screening by whole genome sequencing of single cell extracted from early stage human embryos prior to implantation in IVF clinics (Lorthongpanich et al. 2013; Martin et al. 2013; Zhang et al. 2013). In the latter case, only one or very few cells are available, and sequencing and haplotype accuracy is paramount as the results will directly impact the life of a newborn. Genetic defects in both alleles of the maternal and paternal chromosomes need to be identified with the utmost accuracy.

Before de novo single-cell genome sequencing, the genomic DNA can be amplified. Ideally, the method used amplifies the entire genome from a cell with complete coverage and very little bias. Few technologies are available for this purpose. The commonly used MDA (Multiple Displacement Amplification) method (Dean et al. 2002; Lage et al. 2003) usually results in very large bias in coverage, with up to four orders of magnitude of variation, and frequent dropout of certain sequences. MALBAC (Multiple Annealing and Looping Based Amplification Cycles) (Lu et al. 2012; Zong et al. 2012) and MIDAS (MIcrowell Displacement Amplification System) (Gole et al. Nature Biotech. In press) for whole-genome amplification of single cells are better (Fan et al. 2011; Gole et al. Nature Biotech. In press; Zong et al. 2012), but they still have limitations in terms of sequence coverage and bias, and amplification errors (mutations and creation of chimeras), which are problematic. These result in incomplete assembly, waste, and greater sequencing cost (by one or more orders of magnitude) since many fold coverage is required to acquire the low abundant sequences. Numerous mutations and chimeras also lead to assembly and sequencing errors (Lasken et al. 2007; Voet et al. 2013). In addition, none of these technologies offers mechanisms for resolving haplotypes.

These technologies were derived, at least conceptually, from the seminal rolling circle amplification (RCA) technology (Lizardi et al. 1998). Amplification by RCA is essentially error-free because the same original circular DNA template is repeatedly copied through a rolling circle strand-displacement mechanism from a single primer using a high-fidelity DNA polymerase. We have developed a method for sequence- and length-independent linear DNA amplification using nicking endonuclease-mediated strand displacement amplification (Joneja et al. 2011). The use of nicking endonucleases is not ideal since there are many recognition sequences in the genome. Long Range Strand Displacement Amplification (LR-SDA) technology, described herein, is designed to overcome the limitations described above by using a unique mechanism. LR-SDA is radically different from other methods in that free primers are removed from the reaction solution and no free 3' ends are produced in the process, preventing chimera formation. LR-SDA enables essentially error-free amplification of DNA in very long overlapping fragments, which facilitates the accurate sequencing and haplotyping of genome sequences.

A new generation of sequencing technologies has enabled DNA sequencing at unprecedented high throughput and accuracy, and has also drastically brought down the per-base sequencing cost. What is needed is the ability to acquire contiguity information to phase haplotypes and assemble genomes de novo, and to improve the consensus read accuracy to the point that a genome can be sequenced with complete end to end assembly error-free.

BRIEF SUMMARY OF THE INVENTION

Provided herein is a technological platform which includes novel methods and apparatuses for de novo genome sequencing of single cells with complete haplotype resolution and ultra-high accuracy. The strategy is to replicate the DNA in segments with paired contiguity barcodes to enable unambiguous assembly, and to sequence and assemble both strands of the same DNA molecule independently to improve accuracy. The centerpiece of the platform is a technology which is called "Barcoding Contiguity Replication" (BCR). In BCR, both strands of a double-stranded DNA molecule are replicated in segments and the segments are hardwired with unique contiguity barcodes. Unlike previous methods, replication does not require fragmentation of or any other damage to the original DNA molecule. Once the barcoded segments are sequenced, a simple lookup of the paired barcodes at both ends of the segments allows for the unambiguous connection of the segments and thus the assembly of each strand separately without relying on the alignment of overlapping sequences. The independent sequencing and assembly of both strands of the same DNA molecule provides redundant information for correcting errors and filling gaps, drastically improving the quality of haplotype-resolved assembly and sequencing accuracy. A second technology is a novel method called Long-Range Strand-Displacement Amplification (LR-SDA) for error-free whole-genome amplification of single cells with complete coverage and low bias, again without fragmenting or damaging the original DNA. The long overlapping single-stranded products replicated from both strands of chromosomes are used to feed the BCR sequencing pipeline. The third enabling technology is a microfluidic processor developed to automate BCR and LR-SDA so that sequencing-ready libraries can be prepared from a single cell, or any sample containing cells or genomic material such as RNA or DNA, for off-device sequencing using existing high-throughput sequencing platforms.

The presently disclosed methods enable the duplication of DNA of any length in segments and the addition of a pair of unique barcodes at the ends of any two adjacent segments without fragmenting the original DNA molecule. The presently disclosed methods allow for the amplification of both strands of genomic DNA and subsequent segmental duplication of amplified products from each strand with contiguity barcodes. The barcodes allow for the de novo assembly of the entire individual DNA molecules or chromosomes with long-range or even 100% contiguity. Therefore, the presently disclosed methods enable the de novo sequencing of genome and epigenome using any sequencing technology that can provide sufficient read length to sequence the duplicated segments and the unique barcodes at both ends, or can sequence from both ends and the adjacent parts of each fragment.

The only existing art for the simultaneous fragmentation and tagging of DNA with paired-ended barcodes relies on the fragmentation and tagging of DNA using enzymes, specifically transposase (Steemers, F. et al "Linking sequence reads using paired code tags", Publication number WO 2012/061832 A1. Publication date: May 10, 2012). Other methods for building sequence contiguity mostly rely on dilution of DNA fragments or molecules, and subsequent alignment of the sequenced DNA fragments or molecules, which usually is very problematic for diploid genomes with repeated sequences, e.g. human genome, or even more so for polyploid genomes, e.g. the plant spruce. In the presently disclosed methods, the original DNA is never fragmented and damaged. The same DNA molecule can be used multiple times and subsequent epigenome sequencing or other processes.

The presently disclosed methods offer many advantages over existing arts. (1) The original DNA can be duplicated in segments barcoded with contiguity information without fragmenting or damaging the original DNA and the process can be repeated multiple times. (2) Both strands are duplicated and barcoded independently. Therefore, both strands of a double-stranded DNA can be sequenced and assembled independently. This results in a drastic improvement in sequencing accuracy and the ability to sequence DNA molecules or chromosomes with long-range contiguity or in entirety. (3) The presently disclosed methods allow for the sequencing of epigenomes after the genome has been sequenced and the genomic DNA has been processed (e.g. by disulfite treatment) for detection of chemical modifications. (4) The presently disclosed methods enable the linear amplification of the target DNA without fragmenting or damaging the original DNA. (5) The presently disclosed methods are ideal for genome and epigenome sequencing from single cells. (6) The disclosed microfluidic devices enable the automation of the methodologies. (7) The presently disclosed methods enable the preparation of DNA sample, including amplification and sequencing library construction, for any sequencing platform, including Illumina HiSeq and MySeq platforms, Life Technologies Ion Torrent platforms, Pacific Biosciences SMRT platform, nanopore sequencing and others that may emerge. (8) The disclosed microfluidic devices with polymer barriers are selectively permeable to certain ions and molecules (e.g., $Na^+$, nucleotides, or short oligonucleotides) and enable multistep physical, chemical and biochemical processes to be performed in only one or few microfluidic chambers. Such microfluidic devices are useful, e.g., for repetitive denaturation, hybridization, primer extension, and DNA synthesis, and other assays involving multiple reagent exchanges and washes.

DETAILED DESCRIPTION OF THE INVENTION

I. Introduction

Figure 1:
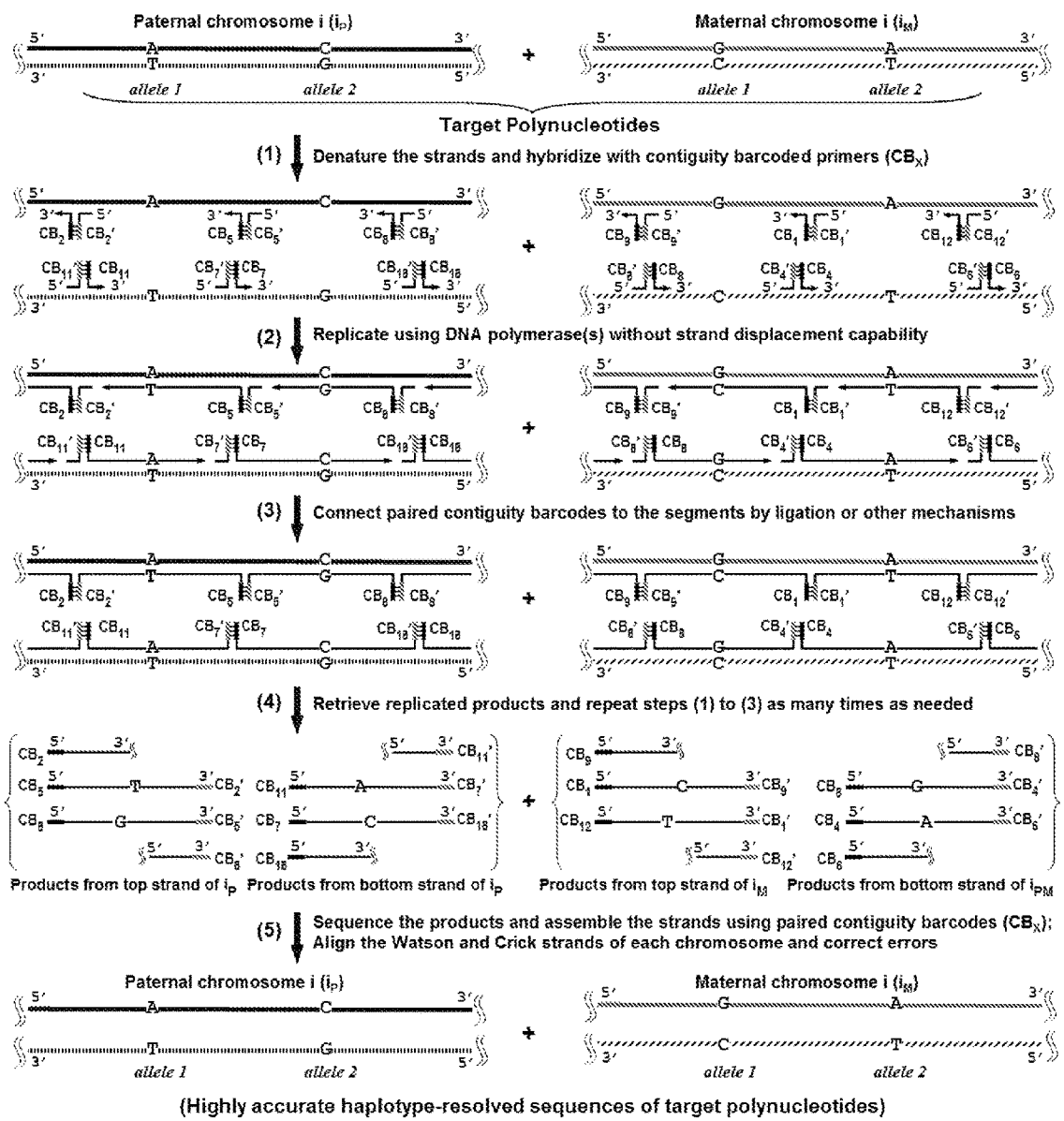
FIG. 1. BCR technology for de novo genome sequencing of single cells. This illustrates how a pair of homologous parental chromosomes can be sequenced with haplotypes resolved. $CB_i$ and $CB_i'$: contiguity barcode pairs with complementary sequences. Each replicated segment has two barcodes at the 3' and 5' ends. The connectivity between the segments is given by the paired barcodes. For example, the top strand of paternal chromosome can be assembled simply by looking up the barcodes at the ends of the fragments and sorting them: —$CB_2$→($CB_2'$—$CB_5$)→($CB_5'$—$CB_8$)→$CB_8'$— and so on. In this example, BCR allows for the assembly of the four individual strands of the two parental homologous haploid chromosomes with complete contiguity, resulting in full haplotype resolution and high per-base sequencing accuracy. The schematic also illustrates the general procedure for barcoding contiguity replication of nucleic acids and how the method is applied to nucleic acid sequencing. The nucleic acids include double-stranded deoxyribonucleic acid (DNA), ribonucleic acid (RNA) and DNA/RNA hybrid, and single-stranded DNA and RNA. If the nucleic acid is DNA, a DNA polymerase is used to replicate the target molecule. If the nucleic acid is RNA, a reverse transcriptase is used to replicate the target molecule. For clarity, a double-stranded target DNA (dsDNA) is used in the illustration herein. Bipartite primers encoded with contiguity barcodes are used to illustrate the general procedure. The detailed procedure entails the following steps: 1) the double-stranded DNA molecule is denatured to separate the two complementary strands. 2) The separated strands are hybridized with a pool of barcoded oligonucleotide primers, each of which contains a primer linked via a universal linker sequence to a unique contiguity barcode sequence. Examples of barcoded primers are described in FIG. 2. 3) The hybridized primers are extended to replicate the target DNA molecules in segments using a polymerase which does not have strand-displacement ability to reach the 5' end of the neighboring downstream primer. The 3'-end of the replicated fragment is then ligated to the 5'-end of the adjacent downstream bipartite barcoded primer. 4) The contiguity barcoded replicated DNA fragments are separated from the original target DNA and retrieved. If needed, step 2 to step 4 are repeated as many times as desired. All the DNA fragments are combined and sequenced using high-throughput DNA sequencing platforms. 5) The sequences are assembled into separate single-stranded DNA using the contiguity barcodes (and overlapping sequences if needed). Errors which are due to sequencing and replication errors are corrected using the redundant sequences from the two individual strands. The two complementary strands are aligned to reconstruct the entire original DNA molecule or genome.

The present disclosure addresses three major challenges in de novo genome sequencing: 1) haplotype phasing and genome assembly; 2) accuracy; and 3) single-cell sequencing. The key concept of the BCR technology is illustrated in FIG. 1. First, the two strands of a double-stranded chromosomal DNA molecule are dissociated and hybridized with a pool of random primers attached with unique contiguity barcodes. The primers are extended to replicate the original DNA molecules. The 3' end of each replicated segment is then connected to the 5' end of the adjacent segment by ligation or other mechanisms. As such, the segments are hardwired with unique paired connectivity barcodes. Once the barcoded segments are retrieved and sequenced using a high-throughput sequencing platform, a simple lookup of the paired barcodes at both ends of the segments allows for the unambiguous connection of the segments and thus the assembly of the entire sequence of each strand separately without relying on the alignment of overlapping sequences. The independent sequencing and assembly of both strands of the same DNA molecule provide redundant information for correcting errors and filling gaps, drastically improving the quality of haplotype-resolved assembly and sequencing accuracy.

The BCR technology inherently works best with very low sample input, preferably from a single or a few cells, therefore is ideal for de novo genome sequencing of single cells because limited input minimizes the depth of coverage required to sequence all the barcoded segments for undisrupted end-to-end assembly of each strand of the chromosomes. In practice, it is unrealistic to expect that entire chromosomes can be replicated without any gaps in one reaction because of potential inefficiency and the stochastic nature of primer hybridization. Fortunately, the original DNA molecules are never fragmented, so multiple rounds of BCR can be performed. At the minimum, there is sufficient coverage to construct long-range scaffolds to facilitate haplotype-resolved assembly. Considering these, the BCR method is augmented with our LR-SDA technology for essentially error-free whole-genome amplification of single cells with complete coverage and low bias. The long overlapping single-stranded products replicated from both strands of chromosomes can be used to feed the BCR sequencing pipeline to provide the bulk of the raw sequencing reads. Moreover, we do not have to exclude the use of sequence alignment since most sequences can be assembled relatively easily by simple alignment.

A paired code tagging strategy has been proposed (Steemers et al. 2012). In the proposed transposase tagging strategy, the paired code tags are inserted into the genomic DNA using engineered transposase enzymes carrying unique paired barcode tags. The genomic DNA is either fragmented or disrupted. In addition to the known issue of sequence preference bias, a significant amount of input materials (10,000 cells or more) is required. Our BCR technology implements the paired code tag strategy in a radically different and more ideal manner. Notably, it has the distinct advantages of not fragmenting the original DNA molecules and low sample input which directly translates into cost saving and higher quality assembly because the depth of sequencing coverage required to retrieve the fragments with paired barcode tags is dramatically reduced. Given sequencing depth, the probability of retrieving any sequences with the paired contiguity barcodes is inversely proportional to the number of cells or copies of DNA molecules used.

BCR is best implemented using a microfluidic processor. A novel microfluidic technology is disclosed herein that enables the next-generation of microfluidic devices (Lee et al. 2013). Selectively permeable polymer barriers with molecularly smooth surfaces are fabricated at desired locations of the microfluidic channels. The permeable polymer barriers allow for the rapid manipulations of cells and biomolecules by electric fields and the seamless implementation of multi-step processes such as enzymatic reactions, washing, solution exchange and biomolecular separation in a single microfluidic chamber. An integrated microfluidic platform, which is used to enable BCR and LR-SDA for de novo genome sequencing of single cells, is also disclosed. Also disclosed is a method for amplifying DNA using polymerase chain reaction (isothermal) in a microfluidic device with selectively permeable polymer barriers.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

A template polynucleotide is a polynucleotide that serves as the template for replication, e.g., by a DNA or RNA polymerase. The template polynucleotide can be genomic RNA or DNA, a plasmid, or a polynucleotide from any source. The template polynucleotide can be double stranded or single stranded. Double stranded template polynucleotides can be denatured prior to replication.

As used herein, the terms "replication," "amplification," "polymerization," "extension" and like terms refer to making at least one copy of a template polynucleotide or its complement. Individual nucleotides are polymerized to form a polynucleotide, typically enzymatically. DNA and RNA polymerases typically rely on a primer, and extend the nascent polynucleotide chain from a primer hybridized to the template polynucleotide. Chemical synthesis can also be used to generate a polynucleotide of random or desired sequence.

An affinity reagent refers to any reagent that specifically binds to its correlate affinity reagent and can be used to separate a target molecule (e.g., nucleic acid) attached to the affinity reagent from non-target material. Examples include biotin and streptavidin, homopolymer nucleic acids (e.g., polyA and polyT stretches), poly-histidine and nickel, GST and glutathione, antibody and antigen (and specifically binding fragments thereof), receptor and ligand (and specifically binding fragments thereof), etc.

The terms "specific for," "specifically binds," and like terms refer to a molecule (e.g., polynucleotide or affinity reagent) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, a primer or affinity reagent that specifically binds to a given target sequence will typically bind the target sequence with at least a 2-fold greater affinity than a non-target sequence. In the case of polynucleotides, specificity is determined by percent complementarity and length of the complementary region.

A "barcode contiguity replication primer" or "BCR primer" refers to a unipartite or bipartite polynucleotide duplex described herein. The BCR primer comprises a barcode, one or two primer sequences (unipartite or bipartite, respectively), optionally an adaptor, and optionally linker sequences connecting the elements. The BCR primer can form a hairpin. For example, the strands at the "top" of the BCR primer (e.g., barcode or adaptor strands) can be joined by a linker. The BCR primer is also referred to as an oligonucleotide pair or duplex DNA assembly herein.

As used herein, the term "unipartite" refers to a BCR primer that has only one primer sequence, i.e., on one of the strands of the duplex DNA assembly. The primer can have a free 3' end to be extended by a polymerase, or a free 5' end to be ligated to a polynucleotide extended from an adjacent BCR primer. "Unipartite" can also refer to a method where only one strand of the BCR primer is incorporated into an extended polynucleotide. The term "bipartite" refers to a BCR primer that has two primer sequences, one on each of the strands of the duplex DNA assembly. A bipartite BCR primer will thus have a free 3' end to be extended, and a free 5' end available for ligation of an extended polynucleotide. "Bipartite" can also refer a method where both strands of the BCR primer are incorporated into an extended polypeptide.

The term "adaptor" refers to a known sequence that can be used for separation, or as a template for an amplification or sequencing primer. Typically, the adaptor will comprise about 4-50, 8-20, or 10-25 nucleotides. The adaptor can also be attached to an affinity reagent.

The term "barcode" refers to a unique polynucleotide sequence (e.g., 4-25, 10-22, 5-15 nucleotides) used to identify the relative location of a polynucleotide sequence on a template polynucleotide. The term can refer to a duplex of single stranded polynucleotides or either individual, complementary strand of the duplex.

A "nucleic acid" or "oligonucleotide" or "polynucleotide" refers to at least two nucleotides covalently linked together. The term nucleotide typically refers to a monomer. Oligonucleotides (e.g., primers) are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid generally contains phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. The ribose-phosphate backbone can be modified for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "probe" or "primer" or "primer sequence" refers to one or more nucleic acid fragments that hybridizes to a polynucleotide of interest (e.g., a template polynucleotide, adaptor, etc.). A probe or primer can be of any length depending on the particular technique it will be used for. For example, PCR primers, or primers for initiating polymerization are generally 4-40 or 10-30 nucleotides in length, while nucleic acid probes are generally longer and can be more than a hundred nucleotides in length. The probe or primer can be unlabeled or labeled (e.g., with an affinity reagent or detectable label). One of skill can adjust the length and complexity of the primer or probe that will hybridize to the targeted polynucleotide to provide optimum hybridization and signal production for a given hybridization procedure, and to provide the required resolution and stringency. One of skill will recognize that the precise sequence of particular primers and probes can be modified to a certain degree or be less than entirely complementary to a targeted polynucleotide, but retain the ability to bind to (e.g., hybridize specifically to) the targeted polynucleotide. For example, primers with random sequences can be generated and used to hybridize to unknown sequences at a lower stringency than a primer with 100% complementarity to a known sequence.

A nucleic acid polymerase "lacking strand displacement activity" refers to a polymerase that essentially does not displace an existing, blocking strand as it travels along a template polynucleotide. Examples include T4, T7, engineered thermophilic Phusion, and Q5 DNA polymerases. One of skill will understand that the term "lacking" is rarely absolute, so that a polymerase lacking strand displacement activity may under certain conditions displace a blocking nucleotide in one out of $10^4$-$10^{12}$ instances. A nucleic acid polymerase having strand displacement activity, on the other hand, does displace an existing, blocking strand as it travels along a template polynucleotide. Examples include Bst DNA Polymerase (Large Fragment), Phi29 DNA polymerase, and Sequenase V2.0.

A permeable polymer barrier refers to a polymeric matrix that is selectively permeable to certain chemical entities or molecules but much less permeable or impermeable to large molecules by simple diffusion or under an electrophoretic force. An example is a polymeric gel matrix of 20% polyacrylamide produced by the polymerization of 19% acrylamide monomer and 1% N,N'-methylenebisacrylamide crosslinking monomer. Such a polymer is permeable to small inorganic and organic ions (for examples, sodium ions, chloride ions, tris(hydroxymethyl)aminomethane, 2-(N-morpholino)ethanesulfonic ions), and small polyelectrolytes (for examples, a 6-20mer oligonucleotides), but is much less or virtually not permeable to large biomolecules such a 1000 nucleotide long DNA molecule. The polymer is usually produced by polymerizing monomers and crosslinkers. Monomers include but are not limited to acrylamide, acrylic acid, lactic acids and their derivatives. Crosslinkers include but are not limited to N,N'-methylenebisacrylamide, diacrylate with polyethylene linker of various lengths (PEG-DA) and bisacrylylcystamine. The monomers and crosslinkers may also be derivatives that contain functional groups, including but not limited to primary amine (—$NH_2$), carboxylate (—COOH), sulfhydryl (—SH), azide (—$N_3$), alkynyl, biotin, maleimide, etc. Polymer barriers with different porosity or permeability can be fabricated by a person of skill in the art by varying the concentration of the monomers and crosslinkers. For example, 5%, 10%, 15%, 20%, 25%, 30%, 40% or higher concentration of polyacrylamide with ratios of acrylamide to bisacrylamide ranging from 100:1, 50:1, 40:1, 30:1, 25:1, 20:1, 10:1, 5:1, 1:1 to 0:1 can be used.

III. BCR Chemistry

As illustrated in FIG. 1, the BCR process is relatively straightforward. The key elements to be considered include: (1) the design and synthesis of the primers with unique contiguity barcodes; (2) replication of the genomic DNA, (3) connection or replication of the barcodes; (4) retrieval and sequencing of the BCR product; and (5) sequence assembly using paired barcode tags.

A. Design and Synthesis of Primers with Contiguity Barcodes and BCR Methods

Figure 2:
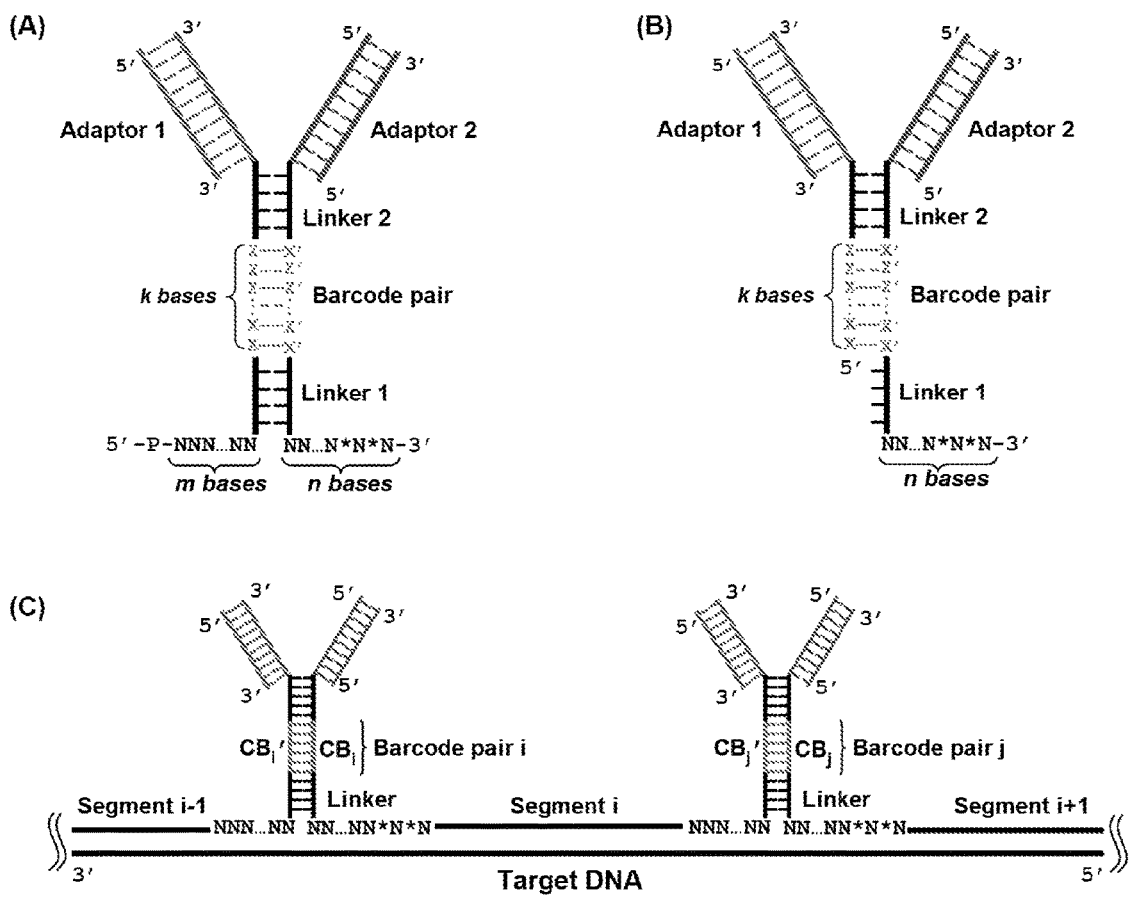
FIG. 2. Contiguity barcoding primers and linkage information. The diagrams illustrate the two design examples of the contiguity barcodes and the concept of how contiguity linkage information is provided by the unique barcode pairs. (A) Bipartite barcodes. (B) Unipartite barcodes. Each contiguity barcode is linked to a primer via a linker sequence. An adaptor sequence can also be included. Each contiguity barcode has a unique sequence, with a length typically between 6 to 30 bases, depending on the specific application. The barcodes are provided as a pool of oligonucleotides with a very large number of unique diverse sequences which are chemically synthesized using a mixture of 1 to 4 bases (A, C, G and T, or other nucleotide analogs) in each position along the sequence. The barcodes always come in pairs, composed of a unique sequence and its reverse complement. Each primer has one of the random or semi-random sequences that are also chemically synthesized using a mixture of 1 to 4 bases (A, C, G and T, or other nucleotide analogs) in each position along the sequence. The length of the primer can be varied, but is typically between 6 to 20 bases. (C). Each pair of barcodes provides the linkage information for the two neighboring DNA segments replicated from the target molecule. The replicated DNA segments can be connected to one another simply by matching the barcodes at both ends of each segment to the segments with the reverse complementary barcodes. In this example, $CB_j'$ and $CB_i$ contiguity barcode pair links segment i−1 to segment i, which is in turn linked to segment i+1 by $CB_j'$ and $CB_j$ contiguity barcode pair.

First, the total number of barcodes has to be sufficient for each barcode pairs to be unique. Assume that the 12 billion bases ($1.2 \times 10^{10}$ bases) of the diploid human genome (literally all the bases in 4 strands for each homologous chromosome pair) replicated in segments with an average length of 600 bases, the total number of segments to be replicated is 20 million ($2\times10^7$). If we provide one million-fold excess of barcodes, the total number of unique codes required is $2\times10^{13}$ (—30 picomoles). In practice, it may be unnecessary to use such a large excess. Even so, this large pool of unique codes can be encoded using 22-base long oligos with random sequences ($4^{22}=1.8\times10^{13}$). 30,000 times of that amount can be produced very inexpensively (<$100) using a 1-mole-scale oligonucleotide synthesis. 10 to 25-base long oligos with random sequences can be used to encode the barcodes. Second, primers with random sequences will be used to hybridize to the target DNA for replication. In most whole-genome amplification strategies such as MDA and DOP-PCR (Arneson et al. 2008; Telenius et al. 1992), random primers with length from 6 to 15 bases are commonly used. Our design is constrained depending on the mechanism for replication and barcode connection. Primers with contiguity barcodes can be designed and synthesized by many methods. Two design examples are depicted in FIG. 2A and FIG. 2B. FIG. 2C illustrates how linkage information is provided by the contiguity barcode pairs. In this example, the paired barcodes $CB_i'$ and $CB_i$ provide the physical linkage information for connecting replicated segment i−1 to replicated segment i, which is in turn linked to replicated segment i+1 by another pair of barcodes $CB_j'$ and $CB_j$.

Figure 3:
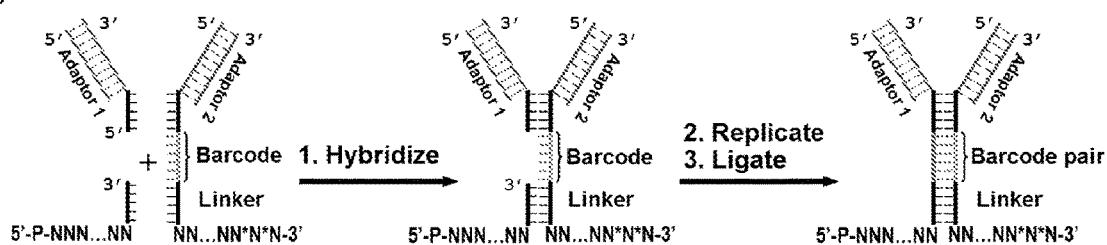
FIG. 3. Synthesis of random primers with paired barcodes. The barcodes come in pairs, each consisting of one unique sequence and its reverse complement. The pairs can be produced prior to use or the complementary barcode can be replicated in the BCR process. (A) Synthesis of bipartite random primers. All oligonucleotides can be chemically synthesized. All oligonucleotides as indicated are hybridized to form the assembly. The replication and ligation of the complementary barcode is carried out as follows: 1) the sequence hybridized to the linker is used as a primer to synthesize the reverse complement barcode by a DNA polymerase; 2) the extended product is ligated to the adaptor sequence. (B) Synthesis of unipartite random primers. In this case, one of the barcode pair is linked to a primer used to replicate the target DNA. In this example, the linker is designed to have a stretch of homopolymer A bases (e.g. 30 A's). A primer (e.g. 25 T's) is hybridized to the poly-A stretch serving as the primer for a DNA polymerase. The barcode is then enzymatically replicated by a DNA polymerase. The replicated barcode is then ligated to the adaptor sequence using a DNA ligase (e.g T4 DNA ligase). The linker oligonucleotide used to replicate the barcodes can be designed to contain features to facilitate its subsequent removal, for examples, several dU's for enzymatic degradation by USER enzymes. (C) Synthesis of contiguity barcoding bipartite primers with a hairpin structure. In this case, the complementary contiguity barcode pair is linked by a hairpin structure. The hairpin sequence can serve as an adaptor. Chemically or enzymatically cleavable bases such as dU bases can be added in the middle of the hairpin sequence for subsequent cleavage of the hairpin structure chemically or enzymatically. For example, cleavage at dU bases can be effected by USER enzymes.
Figure 3:
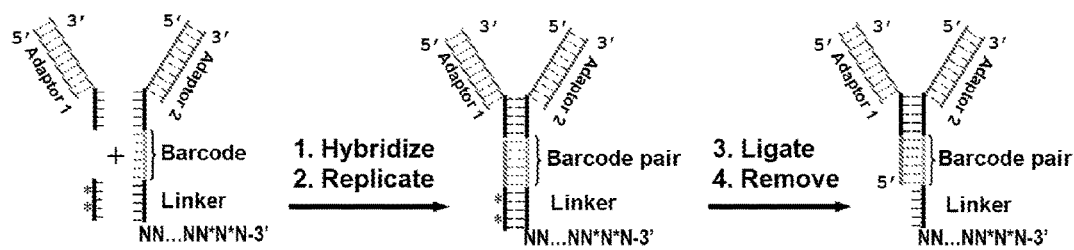
Figure 3:
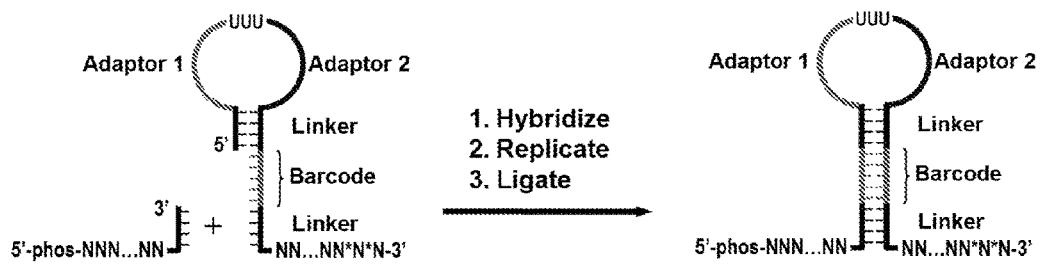

The barcoded primers can be produced by one of skill in the art. Two methods for synthesizing the primers are described schematically in FIG. 3. The primers with contiguity barcodes can be synthesized relatively easily. All oligos can be synthesized chemically. The barcode sequences are replicated by enzymatic DNA synthesis using a common primer that hybridizes to the common linker sequence. The two or more bases from the 3' end are designed to contain a phosphorothioate instead of the normal phosphate diester linkage to render them resistant to removal by the 3' to 5' exonuclease proofreading activity of the DNA polymerases. The adaptor sequences can be designed similarly. The length of the random primers ranges from 6 to 12 bases. Even though not absolutely required, linker and adaptor sequences (e.g. Illumina adaptors) can be added to facilitate downstream processing. The linker sequences can also be used for indexing or tracking the DNA strands. It is understood that other methods can also be used.

Figure 4:
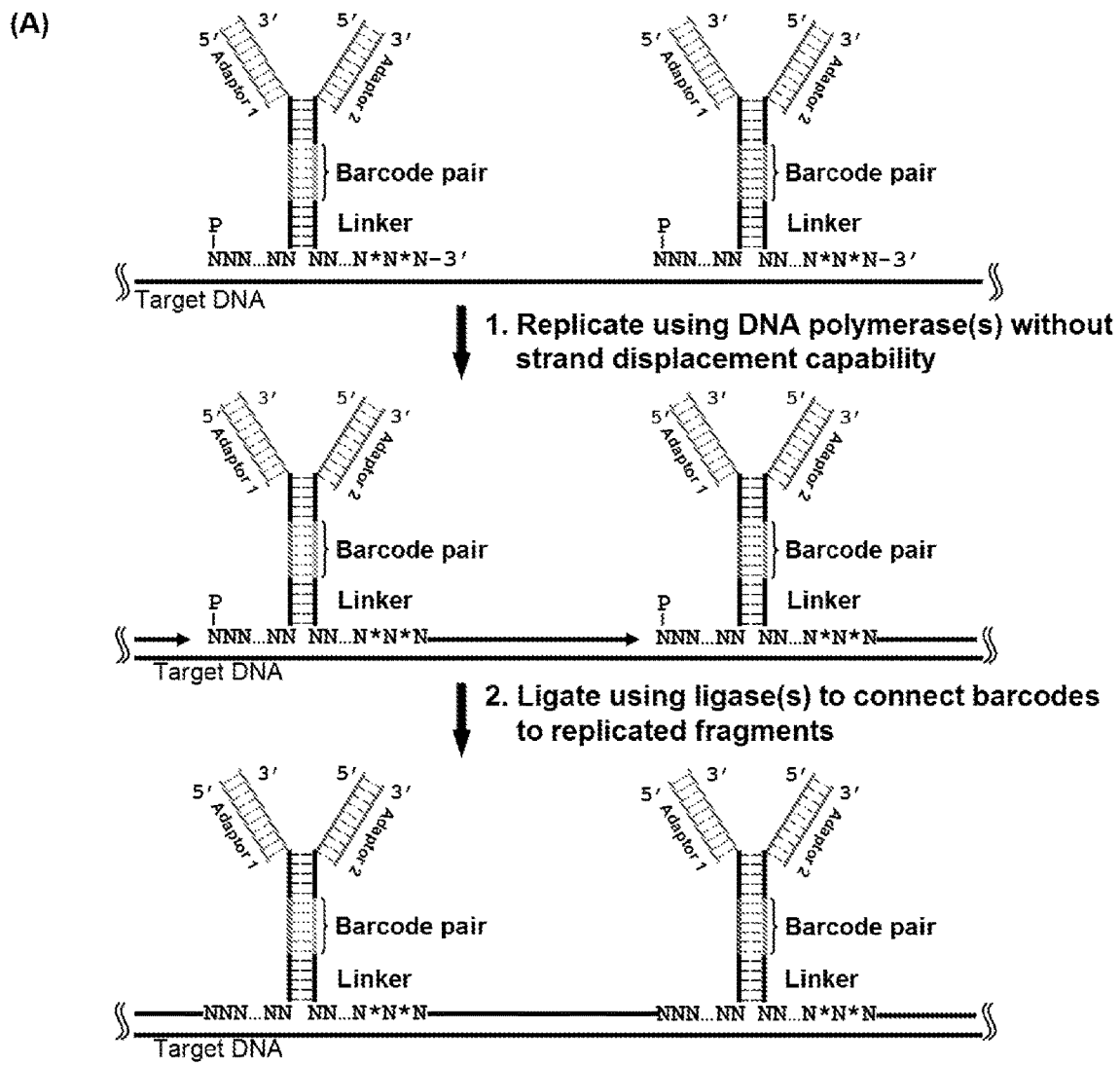
FIG. 4. Bipartite and unipartite methods for BCR. In general, it is preferable to add adaptor and other sequences to the barcoding primers to facilitate and simplify downstream processing such as amplification and sequencing. (A) Bipartite primer approach. Each random primer consists of two sequences held together by the barcode pair and other sequences such as linker and adaptor sequences. The primers are used to replicate the DNA in segments using a DNA polymerase without any strand displacement capability. The 3' end of each replicated segment is then connected to the 5' end of the downstream adjacent segment by ligation. (B) Unipartite primer approach. Each random primer consists of only one sequence and is linked to the barcode and other sequences via a short poly-T (e.g. 25 T's). The primers are used to replicate the DNA. Then, a terminal deoxyribonucleotidyl transferase (TdT) is used to add a short poly-A tail to the 3' end of the replicated fragment. The poly-A is then used as a primer to replicate the linker by a DNA polymerase. The linker is then connected to the barcode sequence by ligation. Alternatively, a DNA polymerase with strand-displacement capability is used to replicate the linker and barcode by strand-displacement DNA synthesis.
Figure 4:
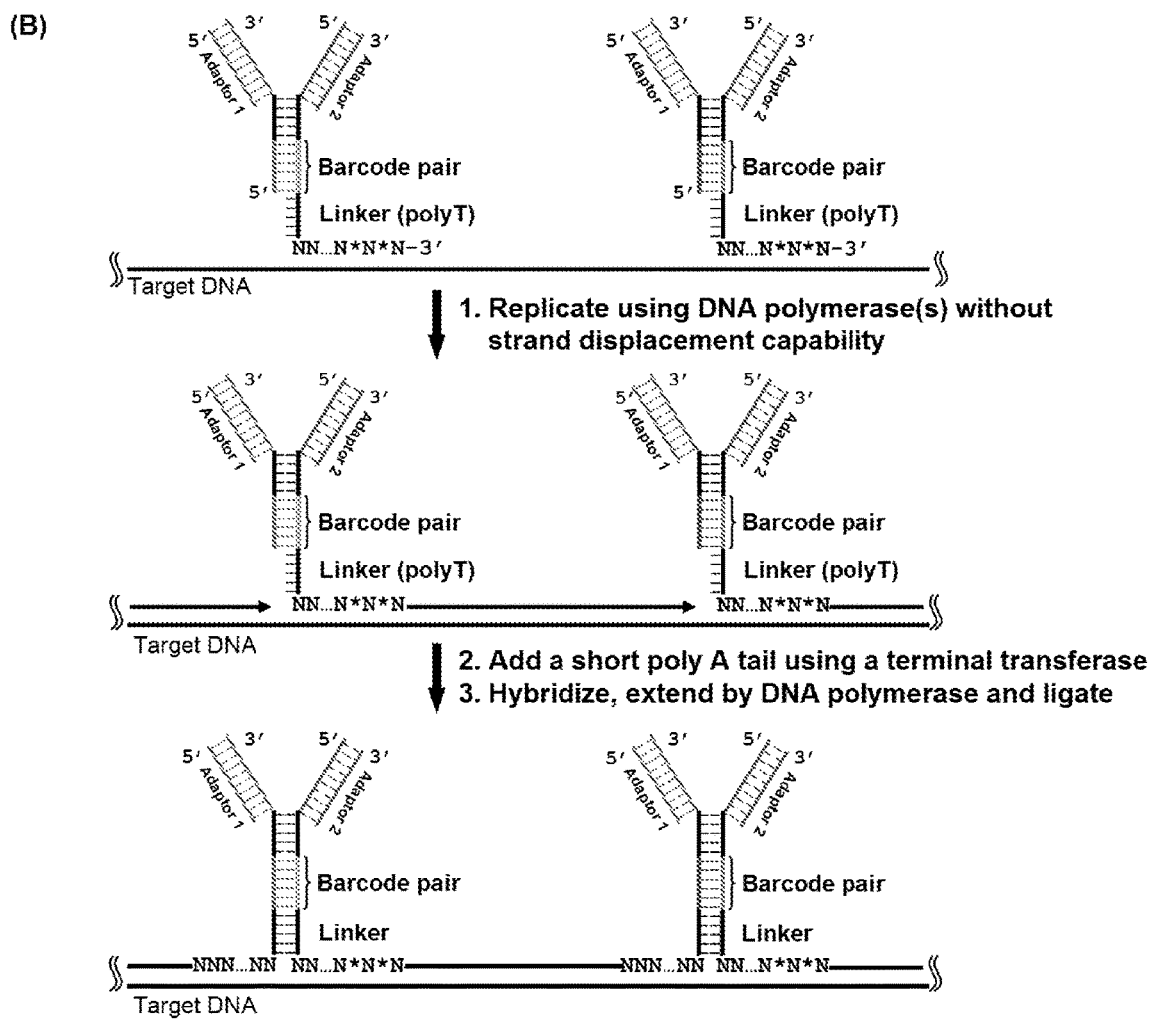

Two methods for BCR are illustrated in FIG. 4. Each method has both advantages and disadvantages. The bipartite approach offers greater simplicity in implementation. The replication and ligation can be carried out in one step. Since each random primer consists of two random sequences, the effective length of the overall priming sequence is perhaps longer and the imperfect hybridization of the two sequences could be an issue. The efficiency of the BCR chemistry depends on primer design, the hybridization process and subsequent enzymatic reactions. Our preliminary studies show success with this method. On the other hand, the unipartite approach offers simpler primer design. Similar to MDA, 6 to 9 bases long random primers will work well. A 25- to 30-base long poly-T can be used as a linker. The challenge is to overcome the inefficiency and variation in the addition of the poly-A tail by the TdT to prime barcode replication by DNA synthesis. Even though polynucleotide tailing by TdT is a commonly used technique, the addition of polynucleotide at 3'-recessed ends is not a highly efficient process, and affects the efficiency of the BCR chemistry. The efficiency of this chemistry can be further optimized and improved. It is understood that other methods can also be used to implement the BCR concept.

In BCR, the DNA polymerases used should not have any strand displacement capability. Many polymerases, including mesophilic T4 and T7 DNA polymerases and engineered thermophilic Phusion and Q5 DNA polymerases, are available for this application. Incidentally, these polymerases have 3'-5' proofreading activity and high fidelity (an error rate of $\sim10^{-6}$, similar to phi29 DNA polymerase). Most DNA polymerases and ligases (e.g. T4 DNA ligase) can efficiently utilize primers as short as 6 bases.

Figure 5:
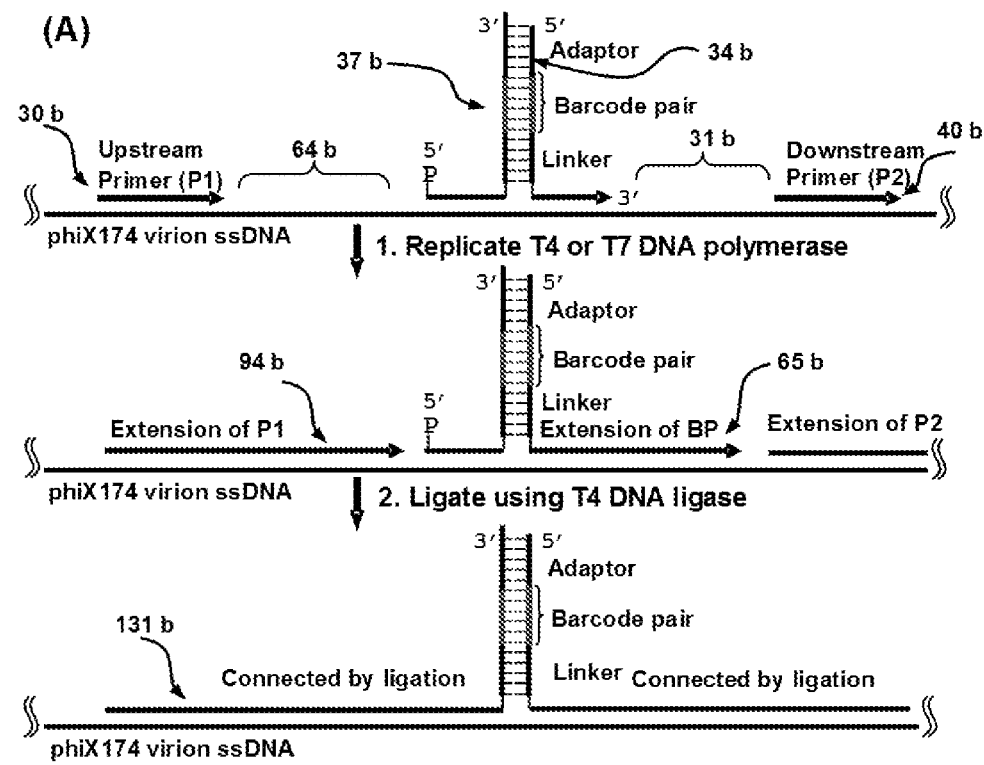
FIG. 5. Examples of BCR using the bipartite method. (A) A model system consisting of phiX174 ssDNA as a template was used to carry out the BCR reaction. The bipartite (BP) primer consists of two 9-base sequences held together by the barcode and sequencing adaptor. One oligo is 34 bases long while the other is 37 bases long. The downstream primer is 30-base long with 5' phophorylated. (B) The primers are hybridized to the template. For the primer extension DNA synthesis, the reaction was performed using T4 DNA polymerase at 12° C. for 10 min, 20° C. for 10 min, and then 37° C. for 2 min. For the extension plus ligation reaction, T4 DNA ligase is then also added along with the T4 DNA polymerase, and reaction was continued at 20° C. for 1 hour after the extension synthesis. After the replication from P1, BP and P2 primers, a 65-base fragment is produced from BP primer (in red box), a 143-base fragment from P1, and a long product from P2. Ligation resulted in two products, a 131-base fragment between P1 and BP, and another very long fragment between BP and P2. (C) A simple ligation using an upstream 20-base primer juxtaposed to the BP primer (Ligation 1 and ligation 2) and 5'-end part of the BP primer (Ligation 3). As can be observed a 57-base product is produced. The BP primer is ligated more efficiently than a single 5'-end part of the bipartite primer. The 20-mer was run out of the gel and not shown on the gel.
Figure 5:
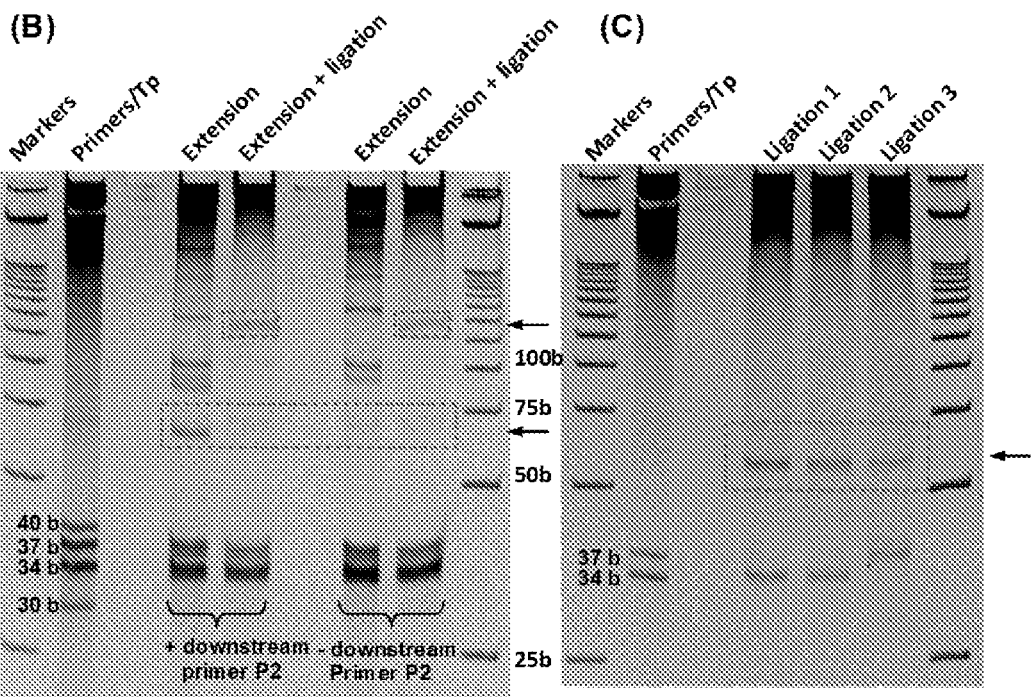

One concern was whether the barcode and adaptor sequences would significantly alter behaviors of the primers such as hybridization and utilization by enzymes. To investigate this issue, a simple model system consisting of 5.4 kb single-stranded circular phiX174 virion DNA and short oligo primers attached to barcode and adaptor sequences was used to test the method. As shown in FIG. 5, the primers can be efficiently utilized by DNA polymerases and DNA ligase and the bipartite approach works well. For the unipartite method, as mentioned above, the addition of polynucleotide by TdT is not as efficient. Similar simple model systems can be used to investigate the various primer designs and enzymatic reactions for the BCR chemistry.

B. Product Recovery and Multi-Cycle BCR

Figure 6:
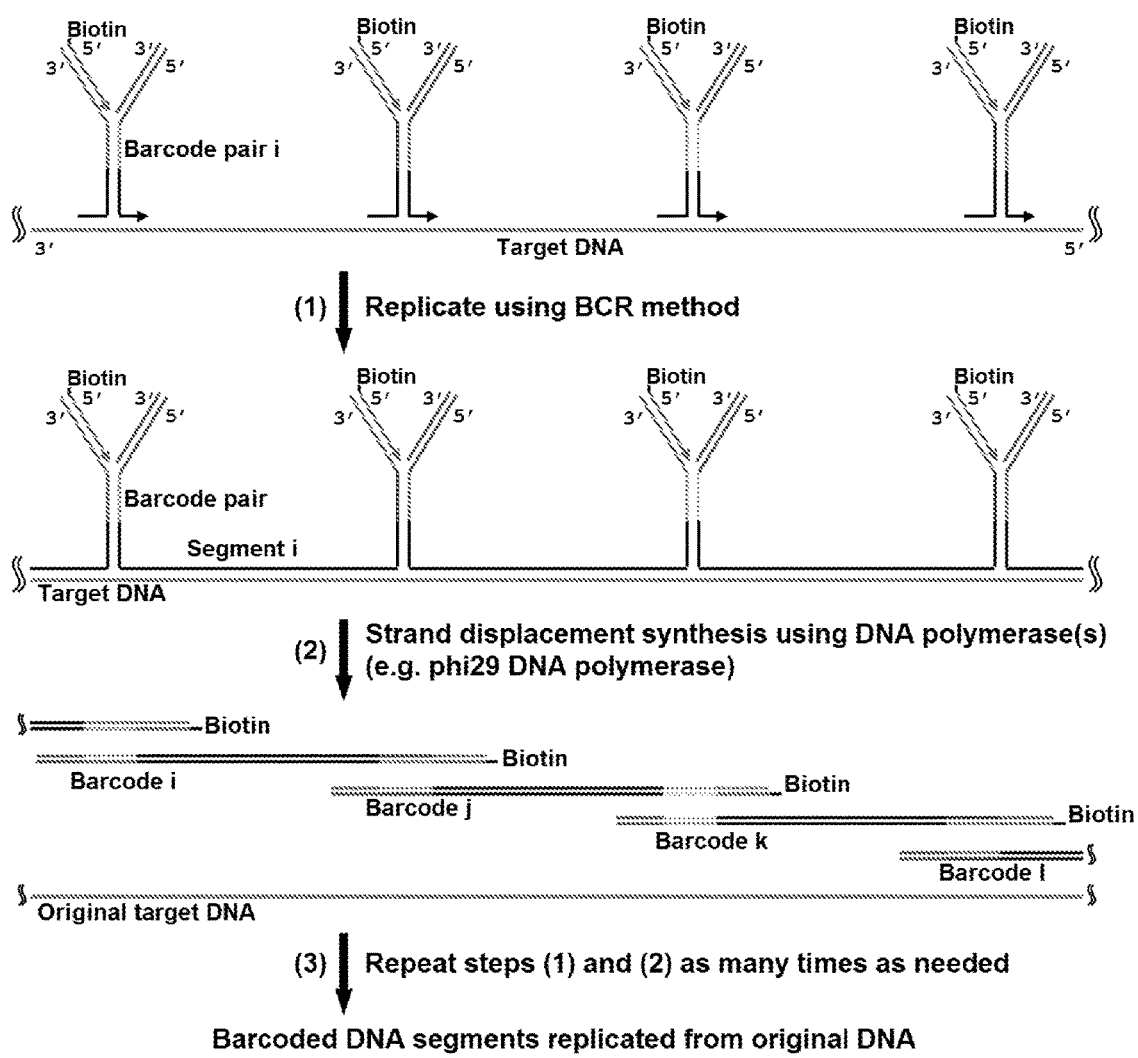
FIG. 6. Method for recovering product and multi-cycle BCR. The replicated fragments are peeled off from the original DNA molecule by a simple strand displacement DNA synthesis using the built-in primer on the adaptor. An affinity tag such as biotin can be attached to the adaptor primer to retrieve the BCR product by affinity capture while leaving the original DNA molecule behind for another round of BCR.

Primers can be designed to facilitate simple recovery of the product. As shown in FIG. 6, a simple strand-displacement reaction using phi29 DNA polymerase converts the product into dsDNA and peels it off from the template. The product is then captured by streptavidin attached on the surface of a polymer barrier of a microfluidic processor as described herein. Once the product is recovered, the original DNA is transported back for another round of BCR. Two or more cycles of BCR are performed on a single cell. The purpose is three fold: 1) to compensate for inefficiency and variation due to the stochastic nature of primer hybridization; 2) to increase the number of templates for downstream processing and sequencing; 3) to provide more redundancy for higher accuracy. However, the number of cycles can be limited to a few cycles (2-10) to maximize the recovery of fragments with paired barcodes given the depth of sequencing coverage.

C. Whole-Genome BCR of Single Cells

The BCR chemistry can be optimized using simple model systems consisting of synthetic oligos and short DNA templates, and then serial dilutions of phiX174 ssDNA. In this case, the characterization of the BCR chemistry requires less than a single lane on the Illumina MySeq or other high throughput sequencing platforms. Various primer designs and BCR chemistry can be characterized very extensively and inexpensively. The performance of the BCR chemistry is evaluated by a set of criteria: 1) the length and positional distribution of the BCR fragments along the DNA molecules; 2) the percentage coverage; 3) the percentage of fragments having matched paired barcodes; and (4) the length of the contig that can be assembled by simple lookup and sorting of the paired barcodes. Once the BCR chemistry is validated, the protocols are used for whole-genome BCR of single human cells with microfluidic processors, described in more detail in Sections V and VI.

D. Summary of BCR

Provided herein are methods for replicating a template polynucleotide that does not fragment or damage the template polynucleotide. In some embodiments, the method comprises (a) contacting the template polynucleotide with a plurality of oligonucleotide pairs, wherein each member of each oligonucleotide pair comprises a unique barcode sequence that hybridizes to its complement on the other member of the oligonucleotide pair, and wherein one or both of the oligonucleotide pairs comprises a primer sequence that hybridizes to the template polynucleotide; (b) contacting the template polynucleotide and plurality of oligonucleotide pairs with a polymerase lacking strand displacement activity and reagents necessary for polymerization, and (c) allowing extension of a polynucleotide strand from the 3' end of the primer sequence to produce an extended polynucleotide comprising the barcode, primer sequence, and a sequence complementary to the template polynucleotide, thereby replicating the template polynucleotide. In some embodiments, each member further comprises an adaptor sequence, optionally attached to an affinity reagent. In some embodiments, each member further comprises at least one linker sequence. In some embodiments, the oligonucleotide pair is joined by a linker to form a hairpin on the end opposite the primer sequence. In some embodiments, step (c) further comprises connecting the extended polynucleotide to the adjacent downstream barcoded primer by enzymatic or chemical ligation if bipartite primers are used for the replication, or connecting the extended polynucleotide to the adjacent downstream barcoded primer by adding a short homopolymer polynucleotide using a terminal deoxyribonucleotide transferase to prime a sequence on the unipartite primer and synthesizing the complementary barcode and adaptor sequences using a DNA polymerase if a unipartite barcoded primers are used for the replication.

In some embodiments, the method further comprises (d) collecting the extended polynucleotides (e.g., using an affinity reagent or according to size, e.g., using a microfluidic device as described herein). In some embodiments, the method further comprises (e) sequencing the extended polynucleotides. In some embodiments, the method further comprises (f) assembling the sequences of the extended polynucleotides based on the unique barcodes.

In some embodiments, the method further includes denaturing the template polynucleotide prior to step (a). In some embodiments, the method further comprises allowing the plurality of oligonucleotide pairs to hybridize to the template polynucleotide, and washing away unhybridized oligonucleotide pairs between steps (a) and (b).

In some embodiments, the template polynucleotide is genomic DNA. In some embodiments, the method further includes detecting methylated or other chemically modified nucleotides on the genomic DNA.

In some embodiments, both members of the oligonucleotide pair comprise a primer sequence that hybridizes to the template polynucleotide. In some embodiments, one member of the oligonucleotide pair comprises a primer sequence that hybridizes to the template polynucleotide. In some embodiments, the primer sequence is a random primer sequence. One of skill will recognize that where random primers are used, only one primer sequence of the oligonucleotide pair will hybridize to the template polynucleotide. In some embodiments, the primers are not random, but are designed to hybridize to known sequences on the templates.

In some embodiments, the adaptor sequence is complementary to a predetermined primer sequence (e.g., for detection, sequencing, or amplification).

IV. LR-SDA Chemistry for Whole-Genome Amplification

Figure 7:
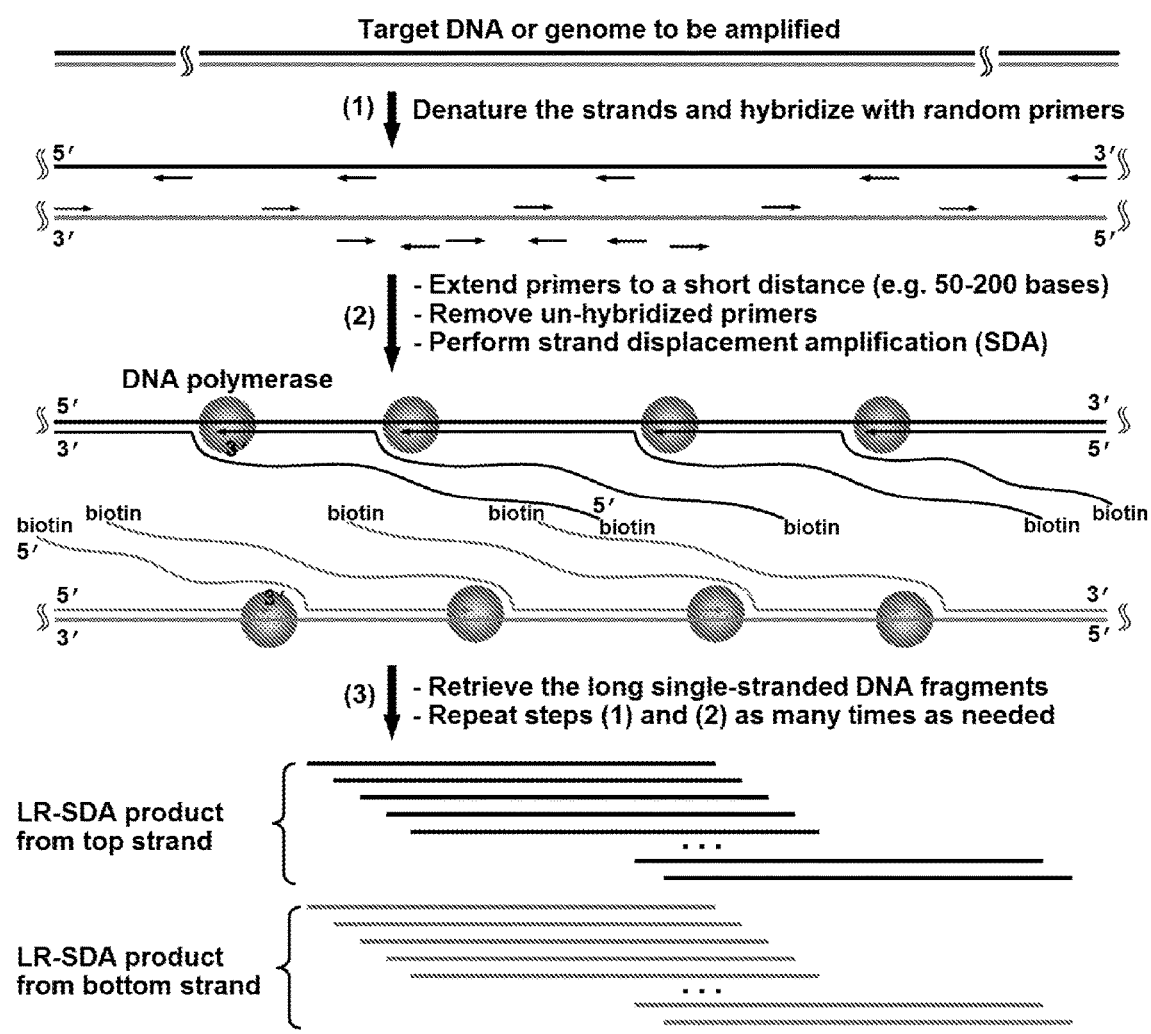
FIG. 7. Basic principle of long-range strand-displacement amplification (LR-SDA). The schematic illustrates a method which is termed long-range strand-displacement amplification (LR-SDA) for replicating a long DNA molecule without fragmenting or damaging the original DNA molecule. The entire process entails the following steps: 1) The double-stranded DNA molecule is denatured and random primers are hybridized to the dissociated ssDNA with the desired average spacing under controlled conditions. The average distance between the adjacent hybridized primers is controlled by using a proper concentration or amount of the total primers. The distance can be between 100 and 2000 bases, or longer if needed. 2) After the hybridized primers are extended a short distance using a DNA polymerase, the excess un-hybridized primers are removed. The target DNA is replicated in overlapping fragments using a DNA polymerase or a combination of different DNA polymerases with high processivity and strong strand-displacement capability. Very long fragments are desirable. The average length can be 50,000 bases or more. 3) The replicated long overlapping DNA fragments are separated from the original DNA templates and collected. This can be performed by denaturing the double-stranded regions using a denaturant (e.g. formamide, KOH) or heat, or both denaturant and heat. The random primers can be designed to contain an affinity tag (e.g. biotin) at the 5' end so that all the replicated fragments carry the affinity tag. The fragments are then separated from the original target DNA by affinity capture. A method and device for such a purpose is described in FIG. 8. If needed, the LR-SDA process can be repeated as many times as desired, and all the amplified products are combined.

The LR-SDA technology is designed to overcome the many limitations of existing methods for whole-genome amplification of single cells, including DOP-PCR, MDA, MALBAC and MIDAS which were described earlier, by using a unique mechanism. The basic principle of LR-SDA is illustrated in FIG. 7. First, the primers are hybridized along the ssDNA in a single event. The long-range strand displacement from the multiple primers by a high-fidelity DNA polymerase results in the amplification of every sequence multiple times. SDA is known to be less sequence dependent, therefore the whole genome can be amplified very uniformly. Second, the long linear ssDNA products are replicated from the original DNA molecule, so the errors produced by the DNA polymerase (with an error rate of $\sim 1\times 10^{-6}$) are not propagated. Assuming that the polymerase errors are randomly distributed, they can be corrected using the redundant coverage, resulting in essentially error-free amplification (consensus error rate $<10^{-18}$ for three-fold coverage). Third, since no free primers are present and no free 3' ends are produced (the product has only free 5' ends), no chimeras can be created. Fourth, the fold coverage and length of the product can be controlled to some degree by spacing the random primers and amplification time. Based on our experience using circular DNA template (equivalent to infinitely long linear DNA), single-stranded product as long as 50 to 100 kb can be easily produced in less than 1 hour. If the primers are spaced an average distance of 500 bases apart and average product length is 50,000 bases, a 100-fold amplification is achieved. Finally, since the original DNA molecule is not fragmented, multiple cycles of LR-SDA can be performed as needed.

LR-SDA is radically different from other methods in that free primers are removed from the reaction solution and no free 3' ends are produced in the process, preventing chimera formation. However, to ensure the initial hybridization of the random primers, it is necessary to use primers in vast excess. Removal of the excess primers can be challenging to implement in practice. Development of the microfluidic technology with polymer barriers that is described herein was in part motivated by this complication (Lee et al. 2013). With this breakthrough microfluidic technology, LR-SDA can be enabled for single-cell whole genome amplification. Primer design is known in the art. Again, to facilitate downstream processing, an affinity tag (e.g. biotin) and optionally adaptor sequence can be attached to the 6 to 12 bases long random primers with endonuclease-resistant phosphorothiate diester linkage at the last two bases at the 3' end. Phi29 DNA polymerase and/or Sequenase V2.0 can be used for the strand displacement synthesis. A circular phiX174 virion DNA template can be used as a model system to optimize the chemistry. The LR-SDA product can be analyzed initially by alkaline gel electrophoresis and single-molecule stretching and imaging. The protocols can be used for LR-SDA of single human cells. Product length and distribution can be quantified by single-molecule stretching and imaging. qPCR can be used to analyze randomly selected regions of the genome to quantify uniformity and coverage. LR-SDA can be developed as a stand-alone technology for many applications. Here, it is used to augment the BCR chemistry by enabling error-free whole-genome amplification. Further experimental detail on whole-genome LR-SDA of single cells using a microfluidic processor is described in section V.3.

Provided herein are methods for amplifying a template polynucleotide that do not fragment or damage the template polynucleotide. In some embodiments, the method comprises (a) contacting the template polynucleotide with a plurality of primers; (b) contacting the template polynucleotide and plurality of primers with a polymerase having strand displacement activity and reagents necessary for polymerization; and (c) allowing extension of a polynucleotide strand from the 3' end of at least one of the plurality of primers hybridized to the template polynucleotide to produce elongated amplification product, thereby amplifying the template polynucleotide.

In some embodiments, the method further comprises denaturing the template polynucleotide before step (a). In some embodiments, the method further comprises allowing the plurality of primers to hybridize to the template polynucleotide, and washing away unhybridized primers between steps (a) and (b). In some embodiments, step (c) comprises allowing extension for a predetermined time to produce partially elongated amplification product, washing away unhybridized primers, adding polymerase having strand displacement activity and reagents necessary for polymerization, and allowing extension to continue.

In some embodiments, the primers are random primers. In some embodiments, each of the primers is attached to an affinity reagent. In some embodiments, the method further comprises affinity purifying the elongated amplification product. In some embodiments, the method further comprises separating the elongated amplification product based on size (e.g., using a microfluidic device as described herein, electrophoresis, or chromatography). In some embodiments, steps (a)-(c) are repeated after removal of the elongated amplification product by affinity purification or separation. In some embodiments, primers with sequences that hybridize to known sequences on the template can be used for selective amplifications.

V. Microfluidic Platform to Enable De Novo Single-Cell Genome Sequencing

Figure 8:
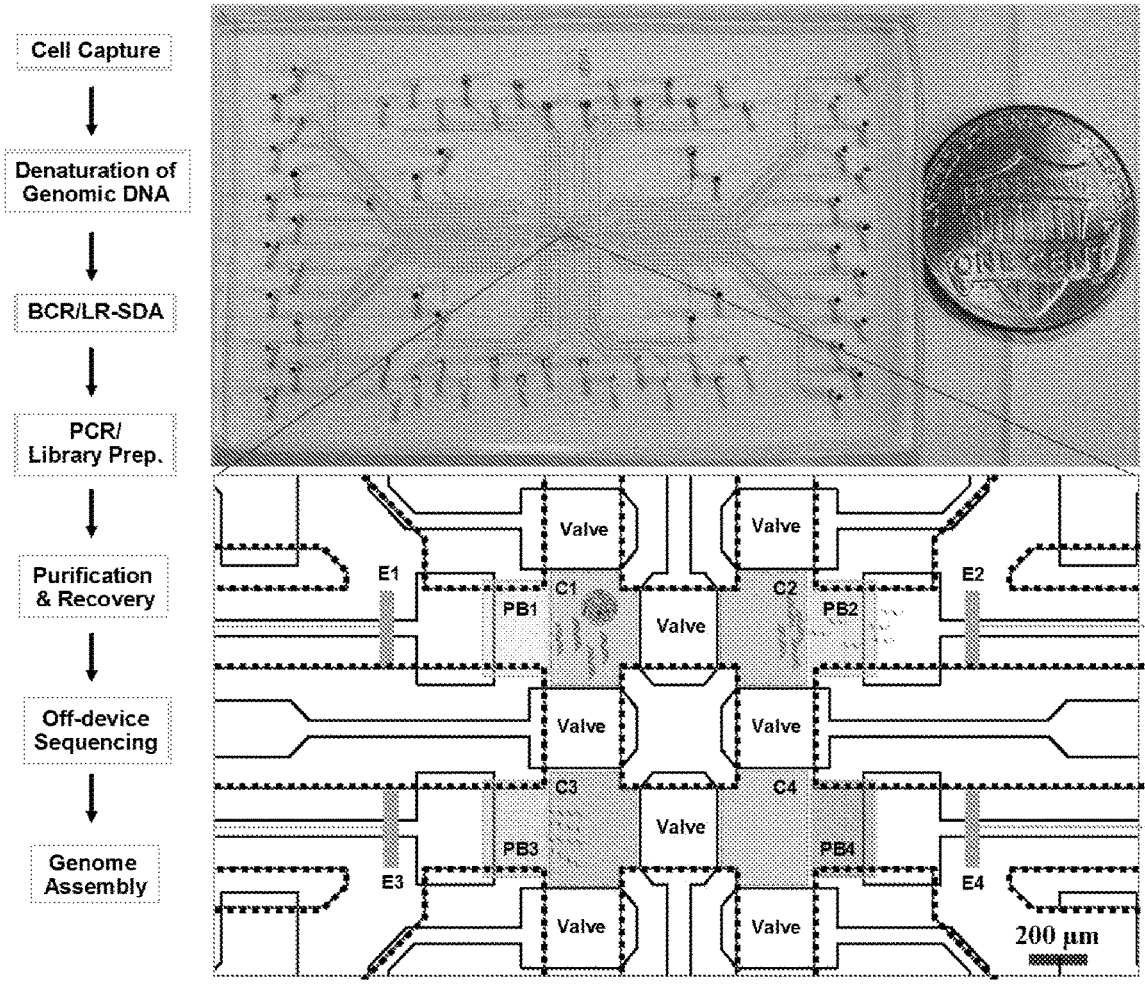
FIG. 8. BCR workflow and microfluidic processor for single-cell genome and epigenome sequencing. Left: Workflow. Top right: Photo of processor with fluid channels (central "I" lines) and valves and valve lines (horizontally extending lines). Bottom right: Illustration of a region with 4 processing chambers. Thick dashed lines: fluid channels on a PDMS layer. Thin black lines: valves and control lines on another PDMS layer. PB1 to PB4: polymer barriers with various permeability and surface functionalities. C1 to C4: processing chambers. E1 to E4: electrodes fabricated on the glass or silicon wafer to which the PDMS layers are bonded. This prototype as shown has 32 inlets/outlets and 4 processing chambers. It can be expanded to include additional modules, such as a hydrodynamic cell trap module and a fractionation module, as needed.

An exemplary BCR workflow is depicted in FIG. 8. Use of a fully automated microfluidic processor is ideal for several reasons: 1) to enable automatic single cell capture and transport; 2) to minimize sample loss by reducing surface to material ratio; 3) to maximize reaction efficiency by using a small reaction volume (Marcy et al. 2007); 4) to enable multi-step processes that are not feasible or cumbersome to carry out in-tube; 5) to eliminate variability due to human operators; and 6) to speed up the process and reduce reagent and labor cost. A microfluidic processor with polymer barriers (FIG. 9 and FIG. 10) can be used (Lee et al. 2013). All processes can be performed in a single processor without the need for sample transfer prior to the amplification step, enabling the rapid, efficient and reliable preparation of sequencing-ready libraries from single cells in a seamless and automated manner.

A. Microfluidic Processor: Overall Design, Fabrication and Operation.

A prototype microfluidic processor with polymer barriers has been designed to enable the entire workflow, from single cell capture, LR-SDA and BCR, to PCR and sequencing library preparation, to be performed in a single compact device. The device consists of a glass slide (1×50×75 mm$^3$), and two polydimethylsiloxane (PDMS) layers, one for valves and one for fluid channels. The valve and channel layers are fabricated and bonded together, and to the glass slide using standard PDMS techniques (Lee et al. 2013; Unger et al. 2000). As illustrated in FIG. 8, at the heart of the device are 4 processing chambers with polymer barriers having the desired selective permeability and functionalities, enabling multi-step processes to be carried out in a single microfluidic compartment. The different polymer microstructures can be fabricated and further functionalized in situ using technology reported in Lee et al. 2013, and optionally fabricating polymer microstructures with molecularly smooth surfaces using only one or no valves. For example, polymer barrier 1 (PB1) can be designed to have very high-density and highly cross-linked polymer only permeable to small charged species such as ions and free nucleotides, and is mainly used for capture and rapid release of cells and DNA, while PB2 is designed to be permeable to only short oligos (e.g. <100 bases) for rapid removal of free primers. PB3 can be functionalized with streptavidin for BCR product recovery while PB4 is designed for fractionation and so on. The polymer microstructures are formed in situ by chemically or photochemically initiated polymerization from monomer solutions trapped at the desired locations using valves or other mechanisms. The combination of acrylamide, bis-acrylamide and polyethylene diacrylate (PEG-DA) as the monomer and crosslinker has been effective. The permeability of the polymer is tuned by varying the concentrations of the monomer and the crosslinker(s). High-density polymer is usually formed with 40% acrylamide, 2% bisacrylamide and 20% PEG-DA. PEG-DA is used to expose PEG moieties on the surface of the barrier to prevent non-specific binding and surface fouling. Such a high-density polymer has pore sizes on the order of a few nanometers or smaller, still permeable to small ions, but virtually impermeable to even short oligos. The polymer is formed with an interface between the aqueous solution and Ar gas, resulting in a molecularly smooth surface. Smaller pore sizes and smooth surface are important in preventing the trapping of DNA molecules, minimizing sample loss. Therefore, for rapid capture and efficient release of DNA, a high-density polymer with PEG linker is used. We have also demonstrated that 1) A 20-30% polymer usually works well for removing short primers and oligos up to 100 bases long, and 2) 10-20% polymer plugs are ideal for fractionation and size selection. Other polymers at various concentrations, and crosslinkers at various ratios can be used depending on the application. Various surface coatings (e.g., with biotin, short oligonucleotides, PEG moieties, primary amine groups, etc.) can be used to reduce non-specific binding, or participate in affinity capture or addition of functional groups.

To apply an electric field or potential, Pt wires are inserted into the inlet/outlets of fluidic flowcell and the desired potential is applied across the selective pair of electrodes. The electrodes (Pt or Au) can also be designed and fabricated onto the glass substrate of the processor similar to what we routinely used for on-chip electrical field manipulations of cells, microbeads and biomolecules (Barbee et al. 2009; Barbee et al. 2010; Hsiao et al. 2010). For temperature control and rapid thermocycling, a high performance custom-built apparatus with Peltier thermoelectric devices controlled via a computer and custom software can be used (Barbee et al. 2011). PDMS valve actuation and fluid flow are driven by pneumatic pressure using a set of solenoid valves and a custom electronic system and software package. The software and the hardware can be upgraded to include more solenoid valves to automate the entire process. In addition, to simplify the operation of the microfluidic processor, a platform can be constructed with pre-configured fluid (tubing connections) and electronic (electrical contacts) interfaces to the processor to allow reliable loading and operation of the device. The device can be further expanded to include additional modules, such as a hydrodynamic cell trap module and fractionation and sample recovery module, as needed. The microfluidic device can be fabricated from plastic, glass, silicon, metal, or other non-PDMS elastomers or flexible polymers.

B. Single-Cell Capture and Multi-Step Processing Using Polymer Barriers.

Figure 9:
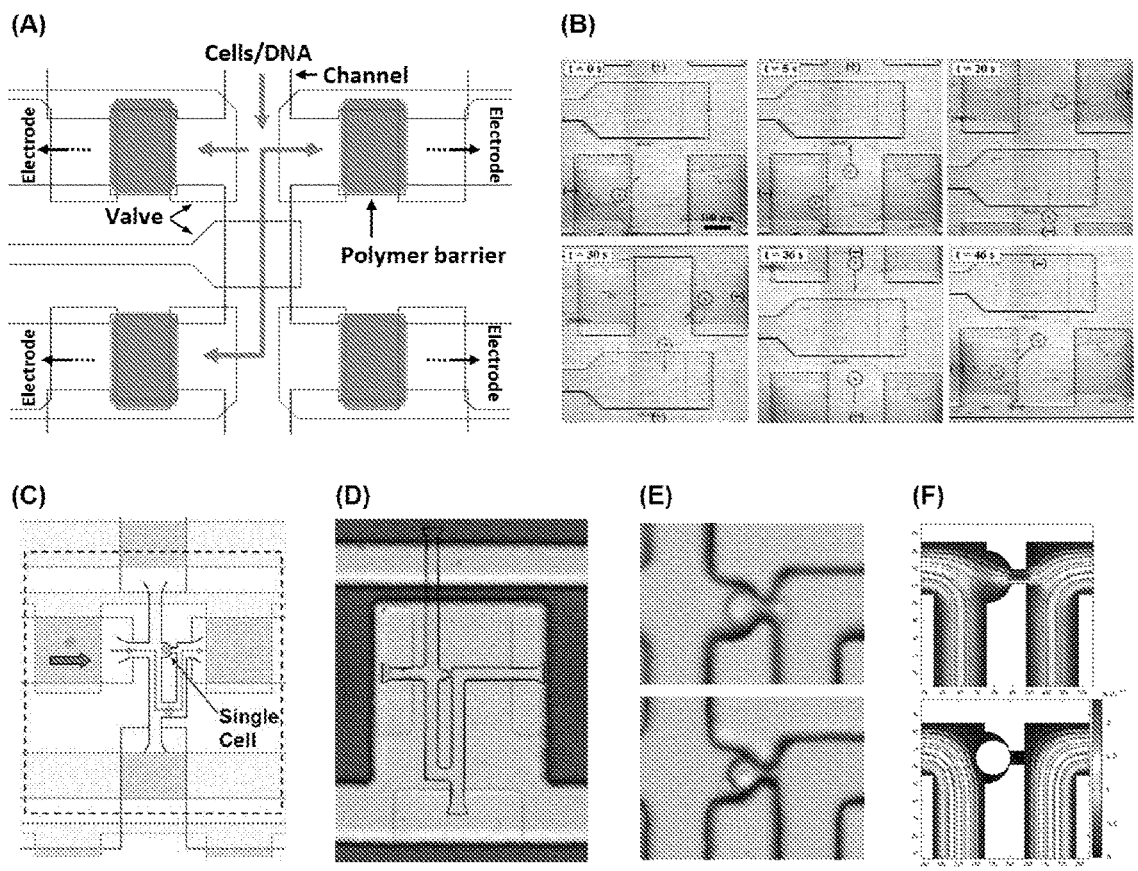
FIG. 9. Microfluidic devices for single-cell trapping by electric field and hydrodynamic flow. (A) A device with 4 polymer barriers. (B) Transport and capture of HeLa cells. (C) A hydrodynamic single cell trap. (D) Single HeLa cell is trapped at the opening of the constriction channel. (E) Trapping of HeLa cells with slightly different sizes. (F): Computational modeling of fluidic flow using finite element analysis (COMSOL). The majority of fluid streamlines are directed into the trap site. Once a single cell enters and is trapped, the streamlines are then redirected to the bypass path.
Figure 10:
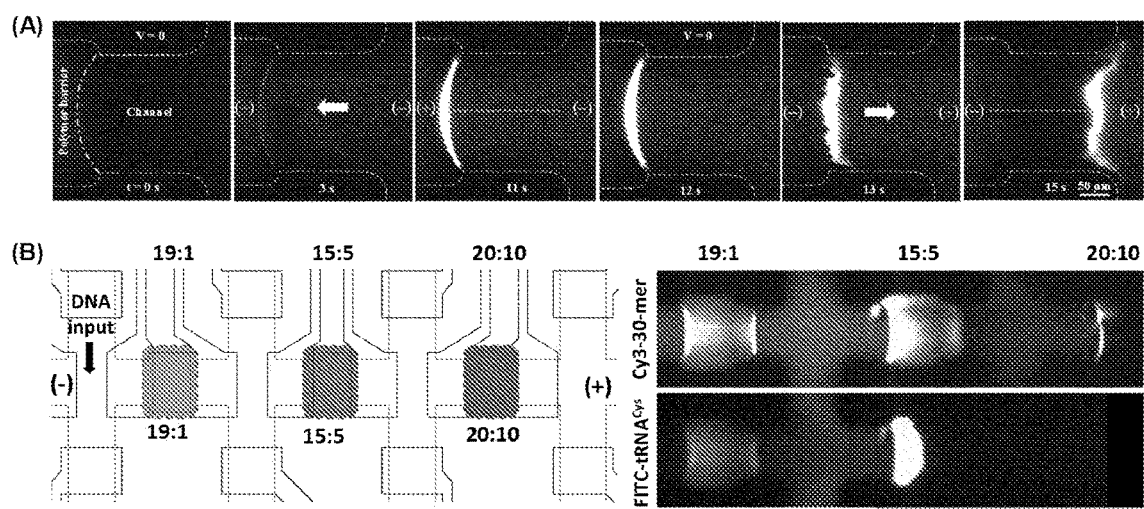
FIG. 10. Microfluidic device for multi-step processing using permeable polymer barriers. (A) Rapid capture, release and transport of λ, genomic DNA by electric fields. The DNA is released and transported as with a group velocity since electrophoretic mobility of DNA in free-solution is length independent. (B) Manipulations of nucleic acids using polymers with different permeabilities. Three polymers were formed using different concentrations of PA (19:1 acrylamide:bis) and PEG-DA: 19% PA+1% PEG-DA, 15% PA+5% PEG-DA and 20% PA+10% PEG-DA. 30-mer oligo can be transported through both 19:1 and 15:5 polymers but not 20:10 polymer while a 76-base tRNA can by transported through 19:1 polymer but not the 15:5 and 20:10 polymers. Snapshots from a movie are shown. This demonstrated that a 30-mer can be separated from a 76-mer tRNA. In addition to polyacrylamide based polymers with various concentrations and ratios of acrylamide monomer and cross-linkers, other polymers such as agarose can be used. The porosity or permeability of the polymer barriers can be tailored to fit the requirements of the specific assay.

We have demonstrated the ability for rapid transport and capture of cells using electric field and hydrodynamic single-cell traps (FIG. 9) (Lee et al. 2013). For simplicity, electric field can be used to capture single cells. Hydrodynamic single cell traps can also be incorporated into the device for ease of automation since a properly designed trap guarantees close to 100% efficiency single-cell capture and allows for the removal of cell-free DNA. We have also demonstrated that multi-step processes can be performed in a single chamber, and the electrophoretic transport of charged biomolecules without solution flow (FIG. 9). DNA can be fractionated by electrophoresis using polymer gel plugs.

Wash and solution exchange are performed by flowing the solution through or into the chamber while the DNA molecules are being held onto the surface of a high-density polymer by an electric field unless stated otherwise. Prior to any reaction, the DNA molecules are released from the surface into the center of the chamber by reversing the electric field briefly. All valves are maintained either open or closed as needed.

To better appreciate how it works, a general procedure is described in detail as follows. The bipartite method (FIG. 4) and the processor shown in FIG. 8 are used to demonstrate the process. (1) A single cell is captured in chamber C1 using electric field. While the field is maintained, a lysis and DNA denaturation solution (e.g. 200 mM KOH+20 mM EDTA+1% SDS) is flowed into the chamber to lyse the cell and dissociate the double-stranded chromosomal DNA molecules. The lysis solution and cell debris are removed by a quick wash while an electric field is maintained across the chamber. (2) The BCR primers are flowed into the chamber and allowed to hybridize to the ssDNA by incubating at the desired temperature (e.g. 12° C.). Optionally, the excess primers can be removed electrophoretically using PB2 in chamber C2 at low temperature (e.g. 0° C.). (3) A reaction mix containing dNTP's, ATP and DNA polymerase and ligase (e.g. T4 DNA polymerase and ligase) is flowed into the chamber to perform the BCR reaction using the desired temperature profile (e.g. 2 minutes each at 4, 12, 25, and then 37° C. for synthesis, and 15 minutes at 22° C. for ligation). (4) After a quick wash, a buffer solution containing phi29 DNA polymerase and dNTP's is flowed into the chamber to perform strand displacement synthesis to peel off the product from the original DNA template. (5) The biotinylated BCR product is captured onto the streptavidin covalently attached to the surface of the polymer (PB3) by transferring the DNA molecules using electrodes E1 and E3. The original chromosomal DNA molecules are then transferred back to chamber C1 for additional rounds of BCR reaction. (6) All BCR products are combined and amplified by PCR using the Illumina sequencing primers in chamber C3. (7) Excess PCR primers are removed using PB4 in chamber C4 and then retrieved using either conventional fluid flow or electrophoretic transfer. The library is sequenced using Illumina MySeq or Hi-Seq systems, or other high-throughput sequencing platforms, such as the Pacific Biosciences' SMRT, Ion Torrent Proton Systems and 454/Roche Pyrosequencers.

C. Summary of Microfluidic Devices

Provided herein are microfluidic devices for running multistep processes requiring reagent exchange, washing, etc. In some embodiments the microfluidic device comprises, (a) at least one chamber, (b) a plurality of fluid channels operably connected to the at least one chamber; (c) at least one polymer barrier separating the inside of the at least one chamber from (i) one of the plurality of fluid channels and (ii) an electrode configured to produce an electric field in the fluid channel and chamber; wherein the at least one chamber includes at least one valve, each valve separating the inside of the at least one chamber from one of the plurality of fluid channels that is not separated from the at least one chamber by the polymer barrier. The polymer barrier is semipermeable (e.g., to ions or nucleotide monomers) and designed to have a size cutoff so that nucleic acids larger than the size cutoff are retained in the at least one chamber when the electrode produces an electric field in the fluid channel of (b)(i) and chamber.

In some embodiments, the microfluidic device is formed from a slide (e.g., glass or plastic) a polymer layer encompassing fluid channels and a polymer layer encompassing at least one chamber. In some embodiments, the polymer is PDMS (polydimethylsiloxane).

In some embodiments, the microfluidic device comprises 2-100 chambers, e.g., 2, 3, 4, 5, 6, 7, 8, 9, 10, or more chambers, each having at least one polymer barrier and at least one valve. In some embodiments, the microfluidic device comprises at least one additional chamber that does not include a polymer barrier.

In some embodiments, the size cutoff of the polymer barrier in each chamber is independently selected. In some embodiments, the at least one polymer barrier has a size cutoff that retains all nucleic acids when the electrode produces an electric field in the fluid channel and chamber. In some embodiments, the at least one polymer barrier has a size cutoff that retains nucleic acids longer than 30 nucleotides. In some embodiments, the at least one polymer barrier has a size cutoff that retains nucleic acids longer than 100 nucleotides. In some embodiments, the at least one polymer barrier has a size cutoff that retains nucleic acids longer than 500 nucleotides.

In some embodiments, the at least one polymer barrier comprises acrylamide, bis-acrylamide, and PEG-DA. In some embodiments, the at least one polymer barrier is coated with an affinity reagent.

Further provided is a microfluidic array comprising 4-$10^8$ (e.g., 100-$10^6$) microfluidic devices.

D. Whole-Genome LR-SDA of Single Cells

Figure 11:
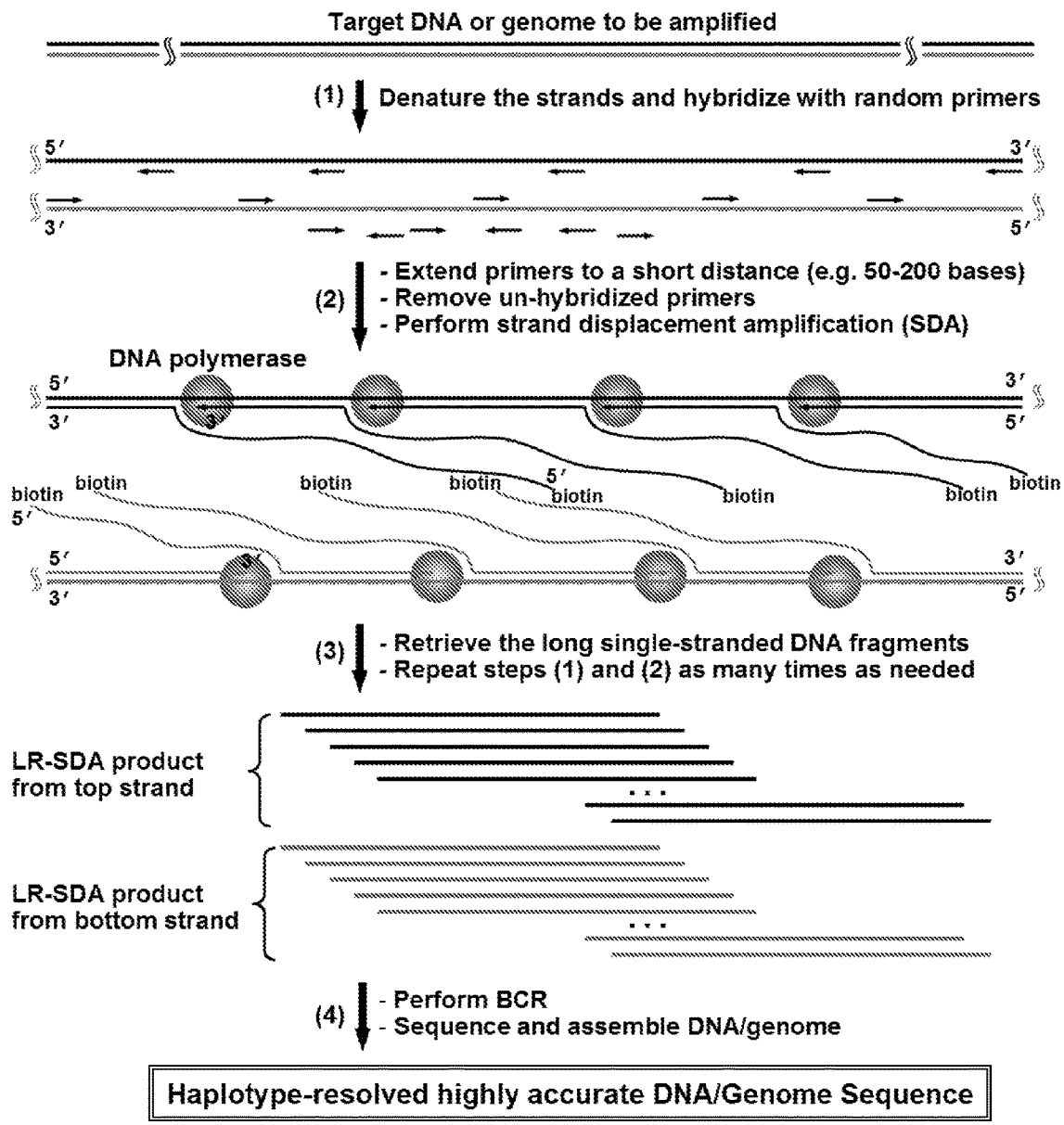
FIG. 11. LR-SDA and BCR for genome sequencing. The schematic illustrates how LR-SDA can be used to amplify the genomic DNA to produce long overlapping DNA fragments from whole genome, which is then used for BCR and genome sequencing.

This entails several steps. (1): Cell capture and DNA denaturation are performed as described above. (2) The random primers are flowed into the chamber and allowed to hybridize to the ssDNA by incubating at the desired temperature or temperature profile (e.g. 12° C., or 30 to 4° C.). (3) A reaction mix containing the DNA polymerase (e.g. T4 DNA Pol) and dNTP's in a buffer is flowed into the chamber and incubated at low temperature (e.g. 4-12° C.) for a brief period to extend the primer a short distance; (4) The excess primers are removed electrophoretically using PB2 in chamber C2 at low temperature (e.g. 0-4° C.). (5) A new reaction mix containing the DNA polymerase and dNTP's is flowed into the chamber to perform LR-SDA at 30-32° C. (5) The LR-SDA molecules are dissociated from the original DNA molecules by flowing in 50 to 200 mM KOH/20 mM EDTA; (6) The biotinylated BCR product is captured onto the streptavidin covalently attached to the surface of polymer (PB3) by transferring the DNA molecules using electrodes E1 and E3. The original chromosomal DNA molecules are then transferred back to chamber C1 for additional rounds of LR-SDA reaction or other processes. (7) BCR reaction is then performed on the LR-SDA product in chamber C3, followed by PCR amplification in chamber C4, and sequenced as described above. The use of LR-SDA to pre-amplify DNA for subsequent BCR and genome sequencing is illustrated in FIG. 11. If BCR is not integrated into the process, the LR-SDA products can be retrieved for subsequent processing and applications. The same methods can be used to amplify genomic material from more than one cell or virion.

Provided herein are methods for amplification (e.g., isothermal or multitemperature amplification) of polynucleotide using fluidic devices as described herein with selectively permeable polymer barriers. In some embodiments, the method comprises: (a) capturing the target polynucleotide onto the surface of a polymer barrier; (b) contacting the captured polynucleotide with a pair of primers under denaturing conditions, for examples in the presence of 20 mM to 200 mM of potassium hydroxide or 8 M urea; (c) hybridizing the primers to the template by replacing the denaturing chemical with a suffer solution suitable for hybridization while the polynucleotide templates and primers are held on the polymer surface by an electric field; (d) contacting the primed template polynucleotide with a polymerase and reagents necessary for polymerization; (e) allowing the extension of a polynucleotide strand from the 3' end of the primer sequence to the end of the polynucleotide template; and (f) repeating (a) to (e) as many times as desired to amplify the template polynucleotide. In some embodiments, a plurality of primer pairs is used to amplify a plurality of template polynucleotides. In some embodiments, the DNA polymerase used has strong strand displacement capability and error proof reading capability. In some embodiments, the length of the target polynucleotide ranges from 50 bases to 100,000 bases (e.g., 50-200, 100-500, 50-1000) or longer.

E. De Novo Genome Sequencing of Single Cells

We have used HeLa cells as a model to develop our single-cell microfluidic technology. The genome of HeLa cell has been sequenced with long-range haplotype resolution using fosmid libraries (Adey et al. 2013). The EBV transformed lymphoblastoid cell line GM20431 can also be used, and it has been sequenced using multiple platforms, including Complete Genomics's standard short reads and LFR (Drmanac et al.; Peters et al. 2012), Illumina SBS short reads on exome and BAC clones (Lo et al. 2013; Peters et al. 2012). Other sequenced cell types can also be used for testing. The presently disclosed methods can be used to sequence any type of genetic material (e.g., viral or cellular).

VI. BCR and LR-SDA for De Novo Epigenome Sequencing of Single Cells

Figure 12:
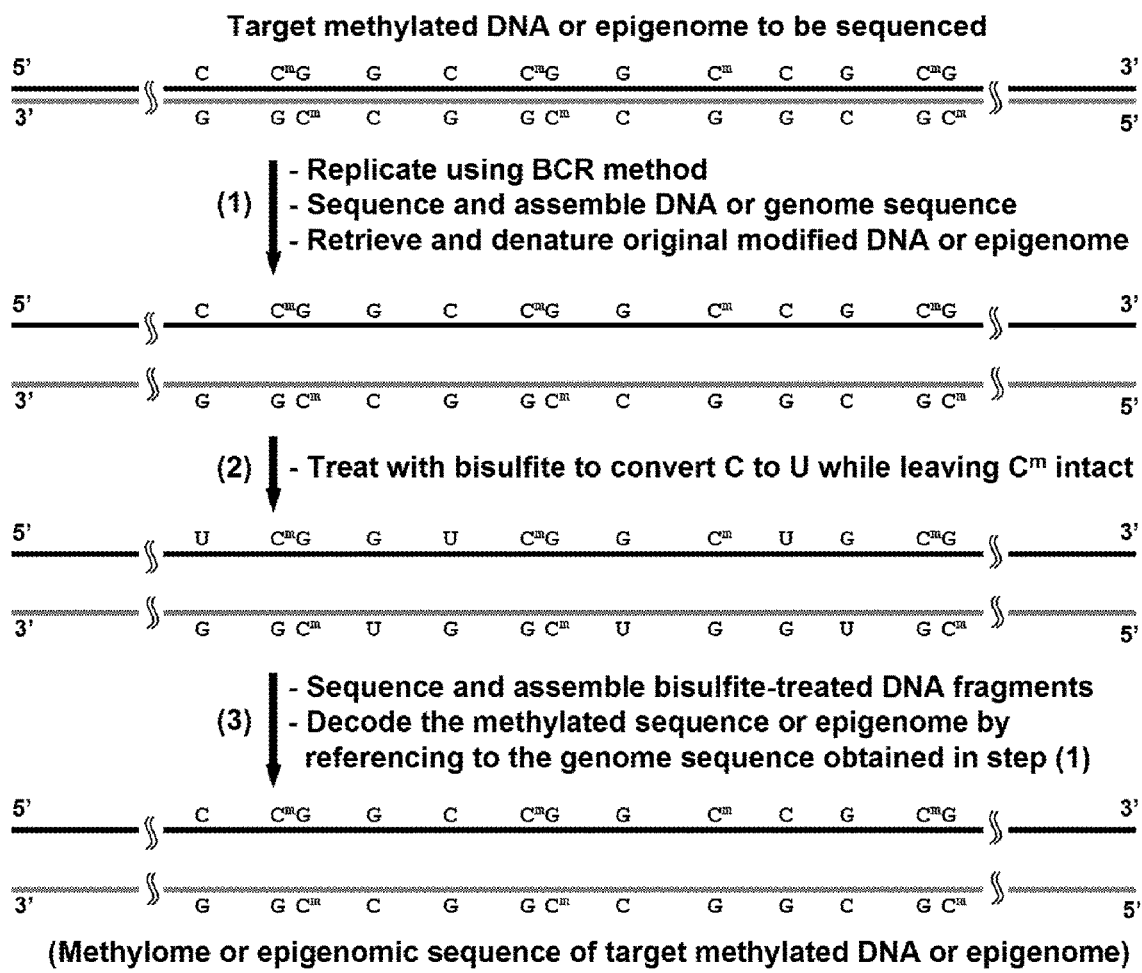
FIG. 12. BCR for epigenome sequencing. The schematic illustrates the general procedure for barcoding contiguity replication of DNA and how the method is applied to epigenomic sequencing. The procedure entails the following steps: (1) The target DNA/genome is sequenced and assembled using the BCR method as described in FIG. 1. (2) The original target DNA is treated with bisulfite according to any standard methods. The bisulfite treatment converts the unmethylated cytosine (C) into a uracil (U) while the methylated cytosine ($C^m$) remains intact. (3) BCR is then performed on the bisulfite-treated genomic DNA and product is sequenced using high-throughput DNA sequencing platforms. The sequences are assembled into separate single-stranded DNA using the contiguity barcodes (and alignment of overlapping sequences if needed). Errors which are due to sequencing and replication errors are corrected using the redundant sequences. Align the two complementary strands to reconstruct the entire DNA molecule or genome. Further error corrects could be made by using the redundant information from the two individual strands. Finally, the methylated C's, or epigenomic sequence is decoded by comparing the bisulfite-treated sequence assembly to the original un-treated sequence assembly.

Due to several very unique characteristics of BCR technology, it is ideal for single-cell epigenome (e.g., methylome) sequencing. First, the original DNA molecules are never damaged or fragmented in the process. As described earlier, the genome sequence with high accuracy and haplotype resolution can first be obtained. This serves as the blueprint or reference for assembling the methylome or epigenome. The original DNA molecules with chemical modified bases are then used for epigenome sequencing. DNA damage and fragmentation are the most common problems associated with bisulfite treatment of DNA. Without an identical genome from the same cell as a reference, it is not feasible to reconstruct the epigenome. The method disclosed here circumvents this problem. Second, since both strands are replicated, sequenced and assembled independently, the redundant information can be used to correct errors due to any inefficiency in the chemical conversion process. Third, by pre-amplifying the original and converted DNA using LR-SDA, sequence coverage can be drastically improved. The basic concept is illustrated in FIG. 12.

Provided herein are methods for sequencing a chemically modified polynucleotide comprising: (a) replicating the modified polynucleotide by BCR without fragmenting or damaging the original modified polynucleotide; (b) sequencing the BCR products and assembling the sequence of the polynucleotide without information on chemical modification on the bases; (c) converting the modified bases in the polynucleotides by chemical or enzymatic means, for example by treatment with bisulfite and other chemicals to convert unmethylated C (cytosine) bases to U (uracil) bases, or treatment with methylation-sensitive restriction endonucleases; (d) replicating and sequencing the converted polynucleotide; (e) determining the sequence of the original modified polynucleotide with information on the modified bases by aligning the converted sequence to the reference sequence determined in (b). In some embodiments, the modified bases to be determined are methylated or hydroxylmethylated cytosine bases.

The examples and embodiments described herein are for illustrative purposes only and that various modifications or changes in light thereof will be suggested to persons skilled in the art and are to be included within the spirit and purview of this application and scope of the appended claims. All publications, patents, patent applications, and database entries cited herein are hereby incorporated by reference in their entireties for all purposes.

VII. Utilities

The present disclosure enables the following methods and apparatuses.

1. A method called "barcoding contiguity replication" (BCR) for replicating nucleic acid with contiguity barcodes without fragmenting or damaging the original nucleic acid molecules.

2. The BCR method to provide physical connectivity information for the replicated DNA sequences to simplify sequence assembly without much computation, in which the sequences are connected or assembled by a simple lookup and ordering of the contiguity barcodes on the sequenced DNA segments.

3. Bipartite BCR primer comprising two short nucleic acid (or analog) sequences, each attached to one of a pair of barcode sequences which are complementary and form a duplex DNA assembly, wherein the two short nucleic acid sequences are random or specific for a target sequence.

4. Unipartite BCR primer comprising a short nucleic acid (or analog) attached to one of a pair of barcode sequences which are complementary and form a duplex DNA assembly.

5. Unipartite BCR primer comprising short nucleic acid (or analog) attached to a barcode sequence, and optionally other linker and adaptor sequences.

6. The duplex assembly of the bipartite primer, each strand independently comprising sequences or elements for downstream processing, including recovery of BCR product, amplification and sequencing.

7. Barcodes for BCR primers comprising DNA and/or RNA and/or nucleic acid analog sequences with a length of 4, 5, 6, 7, 8, 9, 10, 11, 12, 13, 14, 15, 16, 17, 18, 19, 20 bases or longer.

8. Nucleic acid sequence for hybridizing to a target sequence (e.g., template polynucleotide) as part of a BCR primer duplex, wherein the nucleic acid comprises DNA and/or RNA and/or nucleic acid analog with a length of 4, 5, 6, 7, 8, 9, 10, 11, 12, 4-25, 10-30, bases or longer.

9. Pools of the BCR primers with unique barcodes having $10^1$-$10^5$, $10^5$-$10^{50}$, $10^2$-$10^{20}$, $10^5$-$10^{10}$, $10^{10}$-$10^{20}$, $10^{20}$-$10^{25}$, or more unique sequences or molecular species with equal molar ratio.

10. The pool of the BCR primers with unique barcodes having $10^1$-$10^5$, $10^5$-$10^{50}$, $10^2$-$10^{20}$, $10^5$-$10^{10}$, $10^{10}$-$10^{20}$, $10^{20}$-$10^{25}$, or more unique sequences or molecular species with defined molar ratios.

11. Methods for constructing the BCR primers by chemical and enzymatic synthesis where the complementary barcodes are replicated by enzymatic DNA synthesis, followed by ligation.

12. A unipartite method for BCR of nucleic acids in segments without fragmenting or damaging the original molecules, in which the single-stranded target molecule is hybridized with unipartite primers and replicated in segments using a DNA polymerase or polymerases without any strand-displacement capability; the 3' end of the each replicated fragment is extended by a terminal deoxyribonucleotidyl transferase with a homopolymer tail (e.g. 6-20 T's); and a sequence complementary to the homopolymer tail is used to prime the synthesis of the complementary barcode from the adjacent downstream primer.

13. A bipartite method for BCR of nucleic acids in segments without fragmenting or damaging the original molecules, in which the barcoded the single-stranded target molecule is hybridized with bipartite primers and replicated in segments using a DNA polymerase or polymerases without any strand-displacement capability, and then the 3' end of each replicated fragment is ligated to the 5' end of the adjacent downstream bipartite primer using a DNA or RNA ligase.

14. A bipartite method for BCR of nucleic acids in segments without fragmenting or damaging the original molecules, in which the barcoded the single-stranded target molecule is hybridized with bipartite primers and replicated in segments using a DNA polymerase or polymerases without any strand-displacement capability, and then the 3' end of each replicated fragment is ligated to the 5' end of the adjacent downstream bipartite primer by chemical reactions such as click chemistry (e.g., kits commercially available from Jena Bioscience or Life Technologies) or thio-iodo nucleophilic substitution (see, e.g., Montanari et al. (1993) J. Org. Chem. 58:5628).

15. A method for recovering BCR product by strand-displacement synthesis using a primer from the duplex assembly attached to the BCR primer.

16. A method for multi-cycle BCR, in which a multiple rounds of BCR are performed on the same target DNA or RNA molecules.

17. A method called "long-range strand displacement (LR-SDA)" for essentially error-free amplification of DNA with uniform coverage, in which the dissociated single-stranded DNA molecules are hybridized with random or semi-random primers and replicated by long-range strand-displacement DNA synthesis using a DNA polymerase or polymerases with strong strand-displacement capability and high processivity to produce very long overlapping single-stranded DNA fragments.

18. The LR-SDA method, in which the random primers comprise DNA and/or RNA and/or nucleic acid analog sequences with a length of 4, 5, 6, 7, 8, 9, 10, 11, 12, 4-20, 10-30, 15-30 bases or longer.

19. The LR-SDA method, in which the random primers consist of DNA and/or RNA and their analog sequences with a length of 4, 5, 6, 7, 8, 9, 10, 11, 12, 4-20, 10-30, 15-30 bases or longer attached to a adaptor sequence for downstream processing such as affinity capture, amplification and sequencing.

20. The LR-SDA method, in which the free primers are removed after the hybridized random primers have been extended a short distance, e.g. about 20, 10-200, about 30, 40, 50, 10-50, 51-100, 101-200, 50-500 bases, or longer.

21. The LR-SDA method, in which the primers are spaced at an average distance of 20-50, 50-500, 51-100, 101-200, 201-500, 501-1000, 1001-10,000, 10,001-100,000 bases or longer apart by hybridizing the primers under controlled conditions.

22. The LR-SDA method, in which the average length of amplified single-stranded molecules is 50-1000, 100-1000, 1001-2000, 2001-5000, 5001-10,000, 100001-100,000 bases or longer.

23. The LR-SDA method, in which amplified molecules are recovered by using primers attached with an affinity tag such as biotin, and the tagged amplified molecules are captured by affinity capture, for example, the capture of biotinylated molecules by avidin.

24. A multi-cycle LR-SDA method, in which multiple rounds of LR-SDA are performed on the same target DNA molecules.

25. The use of single-stranded product from LR-SDA for BCR and subsequent sequencing.

26. A microfluidic processor with polymer barriers for manipulations of cells and biomolecules.

27. A microfluidic processor with polymer barriers for multi-step processing, including enzymatic reactions, biomolecule capture and separation, in a single or a few microfluidic chambers.

28. A microfluidic processor to enable automated single-cell capture, DNA extraction and replication/amplification, and sequencing library construction for genome and epigenome sequencing of single cells.

29. A method and a device for epigenome sequencing of single cells, in which the genome is first sequenced and assembled using the BCR or LR-SDA/BCR method, then the original DNA molecules are treated with bisulfite and the treated DNA molecules are sequenced and assembled using the BCR or LR-SDA/BCR methodology.

30. A method and apparatus for de novo genome and methylome sequencing of single cells, in which a single cell is captured and sequenced using the BCR or LR-SDA/BCR methodology.

31. A method for haplotype resolution, in which the individual strands from the double-stranded chromosome pairs are replicated by BCR, sequenced and assembled independently.

32. A method for error corrections in genome sequencing for accurate genome sequencing, in which both strands of a double-stranded DNA molecule are dissociated, replicated, sequenced and assembled independently, and the redundant information from the complementary strands is used for error corrections, dramatically improving haplotype and sequencing accuracy.

REFERENCES CITED

Adey, A, Burton, J N, Kitzman, J O, Hiatt, J B, Lewis, A P, Martin, B K, Qiu, R L, Lee, C and Shendure, J. 2013. The haplotype-resolved genome and epigenome of the aneuploid HeLa cancer cell line. *Nature* 500: 207-+.

Arneson, N, Hughes, S, Houlston, R and Done, S. 2008. Whole-Genome Amplification by Degenerate Oligonucleotide Primed PCR (DOP-PCR). *CSH Protoc* 2008: pdb prot4919.

Baday, M, Hastie, A, Cravens, A, Kudeki, D E, Xiao, M and Selvin, P. 2012. Advance High Resolution DNA Mapping Technique to Identify Genomic Variations. *Biophysical Journal* 102: 420a-420a.

Baker, S, Joecker, A, Church, G, Snyder, M, West, J, Salzberg, S, Worthey, E, Smith, T, Wang, J and Reid, J G. 2012. Genome interpretation and assembly-recent progress and next steps. *Nat Biotechnol* 30: 1081-1083.

Barbee, K D, Chandrangsu, M and Huang, X. 2011. Fabrication of DNA polymer brush arrays by destructive micropatterning and rolling-circle amplification. *Macromol Biosci* 11: 607-617.

Barbee, K D, Hsiao, A P, Heller, M J and Huang, X. 2009. Electric field directed assembly of high-density microbead arrays. *Lab Chip* 9: 3268-3274.

Barbee, K D, Hsiao, A P, Roller, E E and Huang, X. 2010. Multiplexed protein detection using antibody-conjugated microbead arrays in a microfabricated electrophoretic device. *Lab Chip* 10: 3084-3093.

Bradnam, K R, Fass, J N, Alexandrov, A, Baranay, P, Bechner, M, Birol, I, Boisvert, S, Chapman, J A, Chapuis, G, Chikhi, R et al. 2013. Assemblathon 2: evaluating de novo methods of genome assembly in three vertebrate species. *Gigascience* 2: 10.

Branton, D, Deamer, D W, Marziali, A, Bayley, H, Benner, S A, Butler, T, Di Ventra, M, Garaj, S, Hibbs, A, Huang, X et al. 2008. The potential and challenges of nanopore sequencing. *Nat Biotechnol* 26: 1146-1153.

Campbell, P J, Stephens, P J, Pleasance, E D, O'Meara, S, Li, H, Santarius, T, Stebbings, L A, Leroy, C, Edkins, S, Hardy, C et al. 2008. Identification of somatically acquired rearrangements in cancer using genome-wide massively parallel paired-end sequencing. *Nature Genetics* 40: 722-729.

Carnevali, P, Baccash, J, Halpern, A L, Nazarenko, I, Nilsen, G B, Pant, K P, Ebert, J C, Brownley, A, Morenzoni, M, Karpinchyk, V et al. 2011. Computational techniques for human genome resequencing using mated gapped reads. *J Comput Biol* 19: 279-292.

Cherf, G M, Lieberman, K R, Rashid, H, Lam, C E, Karplus, K and Akeson, M. 2012. Automated forward and reverse ratcheting of DNA in a nanopore at 5-A precision. *Nat Biotechnol* 30: 344-348.

Clarke, J, Wu, H C, Jayasinghe, L, Patel, A, Reid, S and Bayley, H. 2009. Continuous base identification for single-molecule nanopore DNA sequencing. *Nat Nanotechnol* 4: 265-270.

Dean, F B, Hosono, S, Fang, L, Wu, X, Faruqi, A F, Bray-Ward, P, Sun, Z, Zong, Q, Du, Y, Du, J et al. 2002. Comprehensive human genome amplification using multiple displacement amplification. *Proc Natl Acad Sci USA* 99: 5261-5266.

Dong, Y, Xie, M, Jiang, Y, Xiao, N Q, Du, X Y, Zhang, W G, Tosser-Klopp, G, Wang, J H, Yang, S, Liang, J et al. 2013. Sequencing and automated whole-genome optical mapping of the genome of a domestic goat (Capra hircus). *Nature Biotechnology* 31: 135-141.

Drmanac, R, Sparks, A B, Callow, M J, Halpern, A L, Burns, N L, Kermani, B G, Carnevali, P, Nazarenko, I, Nilsen, G B, Yeung, G et al. 2009. Human genome sequencing using unchained base reads on self-assembling DNA nanoarrays. *Science* 327: 78-81.

Fan, H C, Wang, J, Potanina, A and Quake, S R. 2011. Whole-genome molecular haplotyping of single cells. *Nature biotechnology* 29: 51-57.

Gole, J, Gore, A, Richards, A, Chiu, Y-J, Fung, H-L, Bushman, D, Chiang, H-I, Chun, J, Lo, Y-H and Zhang, K. Nature Biotech. In press. Massively parallel polymerase cloning and genome sequencing of single cells using nanoliter microwells. *Nature Biotechnology*

Hastie, A R, Dong, L L, Smith, A, Finklestein, J, Lam, E T, Huo, N X, Cao, H, Kwok, P Y, Deal, K R, Dvorak, J et al. 2013. Rapid Genome Mapping in Nanochannel Arrays for Highly Complete and Accurate De Novo Sequence Assembly of the Complex *Aegilops tauschii* Genome. *PLoS One* 8:

Hsiao, A P, Barbee, K D and Huang, X. 2010. Microfluidic Device for Capture and Isolation of Single Cells. *Proc Soc Photo Opt Instrum Eng* 7759:

Joneja, A and Huang, X. 2011. Linear nicking endonuclease-mediated strand-displacement DNA amplification. *Anal Biochem* 414: 58-69.

Kalisky, T, Blainey, P and Quake, S R. 2011. Genomic Analysis at the Single-Cell Level. *Annual Review Genetics*, Vol 45 45: 431-445.

Kalisky, T and Quake, S R. 2011. Single-cell genomics. *Nature Methods* 8: 311-314.

Karow, J. (2013), *In Sequence*. GenomeWeb.

Kitzman, J O, Mackenzie, A P, Adey, A, Hiatt, J B, Patwardhan, R P, Sudmant, P H, Ng, S B, Alkan, C, Qiu, R, Eichler, E E et al. 2011. Haplotype-resolved genome sequencing of a Gujarati Indian individual. *Nature biotechnology* 29: 59-63.

Kumar, S, Tao, C, Chien, M, Hellner, B, Balijepalli, A, Robertson, J W, Li, Z, Russo, J J, Reiner, J E, Kasianowicz, J J et al. 2012. PEG-labeled nucleotides and nanopore detection for single molecule DNA sequencing by synthesis. *Sci Rep* 2: 684.

Lage, J M, Leamon, J H, Pejovic, T, Hamann, S, Lacey, M, Dillon, D, Segraves, R, Vossbrinck, B, Gonzalez, A, Pinkel, D et al. 2003. Whole genome analysis of genetic alterations in small DNA samples using hyperbranched strand displacement amplification and array-CGH. *Genome Res* 13: 294-307.

Lam, E T, Hastie, A, Lin, C, Ehrlich, D, Das, S K, Austin, M D, Deshpande, P, Cao, H, Nagarajan, N, Xiao, M et al. 2012. Genome mapping on nanochannel arrays for structural variation analysis and sequence assembly. *Nature Biotechnology* 30: 771-776.

Lasken, R S. 2013. Single-cell sequencing in its prime. *Nature Biotechnology* 31: 211-212.

Lasken, R S and Stockwell, T B. 2007. Mechanism of chimera formation during the Multiple Displacement Amplification reaction. *BMC Biotechnol* 7: 19.

Lee, H S, Chu, W K, Zhang, K and Huang, X. 2013. Microfluidic devices with permeable polymer barriers for capture and transport of biomolecules and cells. *Lab Chip* 13: 3389-3397.

Li, R Q, Zhu, H M, Ruan, J, Qian, W B, Fang, X D, Shi, Z B, Li, Y R, Li, S T, Shan, G, Kristiansen, K et al. 2010. De novo assembly of human genomes with massively parallel short read sequencing. *Genome Research* 20: 265-272.

Lizardi, P M, Huang, X, Zhu, Z, Bray-Ward, P, Thomas, D C and Ward, D C. 1998. Mutation detection and single-molecule counting using isothermal rolling-circle amplification. *Nat Genet* 19: 225-232.

Lo, C, Liu, R, Lee, J, Robasky, K, Byrne, S, Lucchesi, C, Aach, J, Church, G, Bafna, V and Zhang, K. 2013. On the design of clone-based haplotyping. *Genome biology* 14: R100.

Lorthongpanich, C, Cheow, L F, Balu, S, Quake, S R, Knowles, B B, Burkholder, W F, Solter, D and Messerschmidt, D M. 2013. Single-Cell DNA-Methylation Analysis Reveals Epigenetic Chimerism in Preimplantation Embryos. *Science* 341: 1110-1112.

Lu, S J, Zong, C H, Fan, W, Yang, M Y, Li, J S, Chapman, A R, Zhu, P, Hu, X S, Xu, L Y, Yan, L Y et al. 2012. Probing Meiotic Recombination and Aneuploidy of Single Sperm Cells by Whole-Genome Sequencing. *Science* 338: 1627-1630.

Ma, Q C, Ennis, C A and Aparicio, S. 2012. Opening Pandora's Box—the new biology of driver mutations and clonal evolution in cancer as revealed by next generation sequencing. *Curr Opin Genet Dev* 22: 3-9.

Manrao, E A, Derrington, I M, Laszlo, A H, Langford, K W, Hopper, M K, Gillgren, N, Pavlenok, M, Niederweis, M and Gundlach, J H. 2012. Reading DNA at single-nucleotide resolution with a mutant MspA nanopore and phi29 DNA polymerase. *Nat Biotechnol* 30: 349-353.

Marcy, Y, Ishoey, T, Lasken, R S, Stockwell, T B, Walenz, B P, Halpern, A L, Beeson, K Y, Goldberg, S M and Quake, S R. 2007. Nanoliter reactors improve multiple displacement amplification of genomes from single cells. *PLoS Genet* 3: 1702-1708.

Martin, J, Cervero, A, Mir, P, Martinez-Conejero, J A, Pellicer, A and Simon, C. 2013. The impact of next-generation sequencing technology on preimplantation genetic diagnosis and screening. *Fertil Steril* 99: 1054-1061 e1053.

Marx, V. 2013. Next-generation sequencing: The genome jigsaw. *Nature* 501: 263-268.

McNally, B, Singer, A, Yu, Z, Sun, Y, Weng, Z and Meller, A. 2010. Optical recognition of converted DNA nucleotides for single-molecule DNA sequencing using nanopore arrays. *Nano Lett* 10: 2237-2244.

Nagano, T, Lubling, Y, Stevens, T J, Schoenfelder, S, Yaffe, E, Dean, W, Laue, E D, Tanay, A and Fraser, P. 2013. Single-cell Hi-C reveals cell-to-cell variability in chromosome structure. *Nature* 502: 59-+.

Navin, N and Hicks, J. 2011. Future medical applications of single-cell sequencing in cancer. *Genome Medicine* 3:

Navin, N, Kendall, J, Troge, J, Andrews, P, Rodgers, L, Mclndoo, J, Cook, K, Stepansky, A, Levy, D, Esposito, D et al. 2011. Tumour evolution inferred by single-cell sequencing. *Nature* 472: 90-94.

Peters, B A, Kermani, B G, Sparks, A B, Alferov, O, Hong, P, Alexeev, A, Jiang, Y, Dahl, F, Tang, Y T, Haas, J et al. 2012. Accurate whole-genome sequencing and haplotyping from 10 to 20 human cells. *Nature* 487: 190-195.

Peters, B A, Kermani, B G, Sparks, A B, Alferov, O, Hong, P, Alexeev, A, Jiang, Y, Dahl, F, Tang, Y T, Haas, J et al. 2012. Accurate whole-genome sequencing and haplotyping from 10 to 20 human cells. *Nature* 487: 190-195.

Potter, N E, Ermini, L, Papaemmanuil, E, Cazzaniga, G, Vijayaraghavan, G, Titley, I, Ford, A, Campbell, P, Kearney, L and Greaves, M. 2013. Single cell mutational profiling and clonal phylogeny in cancer. *Genome Res*

Powell, A A, Talasaz, A H, Zhang, H Y, Coram, M A, Reddy, A, Deng, G, Telli, M L, Advani, R H, Carlson, R W, Mollick, J A et al. 2012. Single Cell Profiling of Circulating Tumor Cells: Transcriptional Heterogeneity and Diversity from Breast Cancer Cell Lines. *PLoS One* 7:

Salzberg, S L, Phillippy, A M, Zimin, A, Puiu, D, Magoc, T, Koren, S, Treangen, T J, Schatz, M C, Delcher, A L, Roberts, M et al. 2012. GAGE: A critical evaluation of genome assemblies and assembly algorithms. *Genome Research* 22: 557-567.

Schmitt, M W, Kennedy, S R, Salk, J J, Fox, E J, Hiatt, J B and Loeb, L A. 2012. Detection of ultra-rare mutations by next-generation sequencing. *Proc Natl Acad Sci USA* 109: 14508-14513.

Steemers, F J, Gunderson, K, Royce, T, Pignatelli, N, Goryshin, I Y, Caruccio, N, Maffitt, M, Jendrisak, J, Amini, S, Kaper, F et al., inventors; Illumina Inc., assignee Linking sequence reads using paired code tags. Patent Application Number, PCT/US2012/059642. WIPO Publication Number, WO 2012/061832 A1, May 10, 2012.

Suk, E K, McEwen, G K, Duitama, J, Nowick, K, Schulz, S, Palczewski, S, Schreiber, S, Holloway, D T, McLaughlin, S, Peckham, H et al. 2011. A comprehensively molecular haplotype-resolved genome of a European individual. *Genome research* 21: 1672-1685.

Tabor, S and Richardson, C C. 1989. Selective inactivation of the exonuclease activity of bacteriophage T7 DNA polymerase by in vitro mutagenesis. *J Biol Chem* 264: 6447-6458.

Telenius, H, Carter, N P, Bebb, C E, Nordenskjold, M, Ponder, B A and Tunnacliffe, A. 1992. Degenerate oligonucleotide-primed PCR: general amplification of target DNA by a single degenerate primer. *Genomics* 13: 718-725.

Treangen, T J and Salzberg, S L. 2012. Repetitive DNA and next-generation sequencing: computational challenges and solutions. *Nature Reviews Genetics* 13: 36-46.

Unger, M A, Chou, H P, Thorsen, T, Scherer, A and Quake, S R. 2000. Monolithic microfabricated valves and pumps by multilayer soft lithography. *Science* 288: 113-116.

Voet, T, Kumar, P, Van Loo, P, Cooke, S L, Marshall, J, Lin, M L, Esteki, M Z, Van der Aa, N, Mateiu, L, McBride, D J et al. 2013. Single-cell paired-end genome sequencing reveals structural variation per cell cycle. *Nucleic Acids Research* 41: 6119-6138.

Voet, T, Kumar, P, Van Loo, P, Cooke, S L, Marshall, J, Lin, M L, Zamani Esteki, M, Van der Aa, N, Mateiu, L, McBride, D J et al. 2013. Single-cell paired-end genome sequencing reveals structural variation per cell cycle. *Nucleic Acids Res* 41: 6119-6138.

Wallace, E V, Stoddart, D, Heron, A J, Mikhailova, E, Maglia, G, Donohoe, T J and Bayley, H. 2010. Identification of epigenetic DNA modifications with a protein nanopore. *Chem Commun (Camb)* 46: 8195-8197.

Wang, J B, Fan, H C, Behr, B and Quake, S R. 2012. Genome-wide Single-Cell Analysis of Recombination Activity and De Novo Mutation Rates in Human Sperm. *Cell* 150: 402-412.

Wanunu, M. 2012. Nanopores: A journey towards DNA sequencing. *Phys Life Rev* 9: 125-158.

Wanunu, M, Morrison, W, Rabin, Y, Grosberg, A Y and Meller, A. 2010. Electrostatic focusing of unlabelled DNA into nanoscale pores using a salt gradient. *Nat Nanotechnol* 5: 160-165.

Zhang, C, Chen, S, Yin, X, Pan, X, Lin, G, Tan, Y, Tan, K, Xu, Z, Hu, P, Li, X et al. 2013. A single cell level based method for copy number variation analysis by low coverage massively parallel sequencing. *PLoS One* 8: e54236.

Zong, C, Lu, S, Chapman, A R and Xie, X S. 2012. Genome-wide detection of single-nucleotide and copy-number variations of a single human cell. *Science* 338: 1622-1626.

What is claimed is:

1. A method for sequencing a template polynucleotide comprising:
   (a) contacting the template polynucleotide with a plurality of oligonucleotide pairs, wherein each member of each oligonucleotide pair comprises (i) an adaptor sequence, (ii) a unique barcode sequence that hybridizes to its complement on the other member of the oligonucleotide pair, and wherein one or both of the oligonucleotide pairs comprises (iii) a primer sequence that hybridizes to the template polynucleotide;
   (b) contacting the template polynucleotide and plurality of oligonucleotide pairs with a polymerase lacking strand displacement activity and reagents necessary for polymerization, and
   (c) allowing extension of a polynucleotide strand from the 3' end of the primer sequence to produce an extended polynucleotide comprising components (i)-(iii) and a sequence complementary to the template polynucleotide;
   (d) collecting the extended polynucleotides;
   (e) sequencing the extended polynucleotides; and
   (f) assembling the sequences of the extended polynucleotides based on the unique barcodes, thereby sequencing the template polynucleotide, wherein the method does not include fragmenting the template, damaging the polynucleotide or removing epigenetic markers on the template polynucleotide.

2. The method of claim 1, further comprising denaturing the template polynucleotide before step (a).

3. The method of claim 1, further comprising allowing the plurality of oligonucleotide pairs to hybridize to the template polynucleotide, and washing away unhybridized oligonucleotide pairs between steps (a) and (b).

4. The method of claim 1, wherein each member of the oligonucleotide pair further comprises (iv) at least one linker sequence, and the extended polynucleotide comprises components (i)-(iv) and a sequence complementary to the template polynucleotide.

5. The method of claim 1, wherein the template polynucleotide is genomic DNA.

6. The method of claim 5, further comprising detecting methylated bases on the genomic DNA.

7. The method of claim 1, wherein both members of the oligonucleotide pair comprise (iii) a primer sequence that hybridizes to the template polynucleotide.

8. The method of claim 1, wherein the primer sequence (iii) is a random primer sequence.

9. The method of claim 1, wherein the adaptor sequence is complementary to a predetermined primer sequence.

10. The method of claim 1, wherein the adaptor sequence is attached to an affinity reagent.

* * * * *

UNITED STATES PATENT AND TRADEMARK OFFICE
CERTIFICATE OF CORRECTION

PATENT NO. : 10,428,373 B2  
APPLICATION NO. : 15/035957  
DATED : October 1, 2019  
INVENTOR(S) : Xiaohua Huang Page 1 of 1

It is certified that error appears in the above-identified patent and that said Letters Patent is hereby corrected as shown below:

In the Claims

At Column 30, Line 2, after "template" please insert --polynucleotide--.

At Column 30, Line 2, after "damaging the", insert --template--.

Signed and Sealed this  
Tenth Day of December, 2019

Andrei Iancu  
*Director of the United States Patent and Trademark Office*